US009744520B2

(12) United States Patent
Rosseinsky et al.

(10) Patent No.: US 9,744,520 B2
(45) Date of Patent: Aug. 29, 2017

(54) METAL-ORGANIC FRAMEWORKS

(71) Applicant: THE UNIVERSITY OF LIVERPOOL, Liverpool (GB)

(72) Inventors: Matthew J. Rosseinsky, Liverpool (GB); Catherine G. Perkins, Liverpool (GB); John Edward Warren, Liverpool (GB); Kim Elizabeth Jelfs, Liverpool (GB); Paul Boldrin, London (GB)

(73) Assignee: THE UNIVERSITY OF LIVERPOOL, Liverpool (GB)

( * ) Notice: Subject to any disclaimer, the term of this patent is extended or adjusted under 35 U.S.C. 154(b) by 57 days.

(21) Appl. No.: 14/424,780

(22) PCT Filed: Sep. 3, 2013

(86) PCT No.: PCT/GB2013/052304
§ 371 (c)(1),
(2) Date: Feb. 27, 2015

(87) PCT Pub. No.: WO2014/033481
PCT Pub. Date: Mar. 6, 2014

(65) Prior Publication Data
US 2015/0231600 A1 Aug. 20, 2015

(30) Foreign Application Priority Data

Sep. 3, 2012 (GB) .................................. 1215693.1

(51) Int. Cl.
*C07C 7/12* (2006.01)
*C07C 51/347* (2006.01)
*C07C 63/331* (2006.01)
*B01J 20/22* (2006.01)
*B01J 20/30* (2006.01)

(52) U.S. Cl.
CPC ......... *B01J 20/226* (2013.01); *B01J 20/3085* (2013.01); *C07C 7/12* (2013.01); *C07C 51/347* (2013.01); *C07C 63/331* (2013.01)

(58) Field of Classification Search
None
See application file for complete search history.

(56) References Cited

U.S. PATENT DOCUMENTS

| 2004/0200758 | A1* | 10/2004 | Yang ...................... B01J 20/186 208/208 R |
| 2009/0005243 | A1 | 1/2009 | Goddard et al. |
| 2012/0004491 | A1* | 1/2012 | Kulprathipanja ......... C07C 7/12 585/828 |
| 2012/0077092 | A1 | 3/2012 | Lee et al. |
| 2012/0172612 | A1 | 7/2012 | Yaghi et al. |
| 2016/0159713 | A1* | 6/2016 | Long ........................ C07C 7/12 556/147 |

FOREIGN PATENT DOCUMENTS

| WO | 2009011545 | 1/2009 |
| WO | 2011038208 | 3/2011 |
| WO | 2012012125 | 1/2012 |

OTHER PUBLICATIONS

Vermoortele et al.; p-Xylene-Selective Metal—Organic Frameworks: A Case of Topology-Directed Selectivity; Journal of the American Chemical Society; (2011), 133, pp. 18526-18529.
Farha et al; Control over Catenation of Metal—Organic Frameworks via Rational Design of the Organic Building Block; Journal of the American Chemical Society; vol. 132, No. 3, (2010), pp. 950-952, American Chemical Society.
Farha et al; An Example of Node-Based Postassembly Elaboration of a Hydrogen-Sorbing, Metal-Organic Framework Material; Inorganic Chemistry, vol. 47, No. 22, (2008), pp. 10223-10225.
PCT International Search Report, International Application No. PCT/GB2013/052304, May 28, 2014, 4 pages.
Alaerts, Luc et al., Selective adsorption and separation of xylene isomers and ethylbenzene with the microporous vanadium(IV) terephthalate MIL-47, Metal—Organic Frameworks, Angewandte Chemie-International Edition, 2007, 46, 23, pp. 4293-4297, DOI: 10.1002/anie.200700056, Wiley-VCH Verlag GmbH & Co. KGaA, Weinheim.
Bellat, Jean-Pierre et al., Adsorption of gaseous p-xylene and m-xylene on NaY, KY, and BaY zeolites. Part 2: Modeling. Enthalpies and entropies of adsorption, Zeolites 1995, 15:219-227, Elsevier Science Inc., New York, NY.
Castillo, J. M. et al., Molecular Simulation Study on the Separation of Xylene Isomers in MIL-47 Metal-Organic Frameworks, J. Phys. Chem. C 2009, 113, 20869-20874, American Chemical Society.
Chempath, Shaji et al., Molecular Modeling of Binary Liquid-Phase Adsorption of Aromatics in Silicalite, AIChE Journal, Feb. 2004, 463-469, vol. 50, No. 2, American Institute of Chemical Engineers.
Dolomanov, Oleg V. et al., OLEX2: A complete structure solution, refinement and analysis program, Journal of Applied Crystallography, (2009). 42, 339-341, ISSN 0021-8898, doi:10.1107/S0021889808042726, International Union of Crystallography Printed in Singapore.
Finsy, Vincent et al., Pore-Filling-Dependent Selectivity Effects in the Vapor-Phase Separation of Xylene Isomers on the Metal-Organic Framework MIL-47, J. Am. Chem. Soc. 2008, 130, 7110-7118, American Chemical Society.
Greathouse, Jeffery A. et al., Computational screening of metal-organic frameworks for large-molecule chemical sensing, Owner Societies 2010 Physical Chemistry Chemical Physics, 2010, 12, 12621-12629, DOI: 10.1039/c0cp00092b.
Krishna, Rajamani et al., In silico screening of metal-organic frameworks in separation applications, Owner Societies 2011 Physical Chemistry Chemical Physics, 2011, 13, 10593-10616, DOI: 10.1039/c1cp20282k.

(Continued)

*Primary Examiner* — Tam M Nguyen
(74) *Attorney, Agent, or Firm* — Barnes & Thornburg LLP

(57) ABSTRACT

The present invention relates to compounds capable of forming metal-organic frameworks (MOFs), particularly f-block metal MOFs which selectively sorb one component (e.g. para-xylene) from a mixture of components (e.g. m-/p-xylene mixture). The invention also relates to methods of producing and using said compounds.

10 Claims, 11 Drawing Sheets

(56) References Cited

OTHER PUBLICATIONS

Lachet, Veronique et al., Molecular Simulation of p-Xylene and m-Xylene Adsorption in Y Zeolites. Single components and Binary Mixtures Study, Langmuir 1999, 15, 8678-8685, American Chemical Society.

Lima, Ricardo M. et al., Optimal Synthesis of p-Xylene Separation Processes Based on Crystallization Technology, AIChE Journal, Feb. 2009, 354-373, vol. 55, No. 2, DOI 10.1002/aic.11666, Wiley InterScience.

Moreira, Mariana A. et al., Reverse Shape Selectivity in the Liquid-Phase Adsorption of Xylene Isomers in Zirconium Terephthalate MOF UiO-66, Langmuir 2012, 28, 5715-5723, dx.doi.org/10.1021/la3004118, American Chemical Society.

Sheldrick, George M., A short history of SHELX, Acta Crystallographica Section A, Foundations of Crystallography, Acta Cryst. (2008). A64, 112-122, doi:10.1107/S0108767307043930, International Union of Crystallography Printed in Singapore.

Tovbin, Yu. K., The Volume of mieropores and the Dubinin—Radushkevieh equation, Russian Chemical Bulletin, 537-643, vol. 47, No. 4, Apr. 1998, Plenum Publishing Corporation.

United States Environmental Protection Agency, Locating and Estimating Air Emissions From Sources of Xylene, EPA-454/R-93-048, Mar. 1994, 196 pages.

Wantanachaisaeng Puwanat, Capturing Opportunities for Paraxylene Production, 2007, 16 pages, UOP LLC.

Kirk, Cannella W., Xylenes and Ethylbenzene, Kirk-Othmer Encyclopedia of Chemical Technology, 2001, 42 pages, John Wiley & Sons, Inc.

Yang, Cheng-Xiong et al., Metal-Organic Framework MIL-101(Cr) for Separation of Substituted Aromatics, Analytical Chemistry, 2011, 83, 7144-7150, High-Performance Liquid American Chemical Chromatographic Society.

* cited by examiner

METAL-ORGANIC FRAMEWORKS

CROSS-REFERENCE TO RELATED APPLICATIONS

This application is a national stage entry under 35 USC §371(b) of PCT International Application No. PCT/GB2013/052304, filed Sep. 3, 2013, and claims the benefit of United Kingdom Patent Application No. 1215693.1, filed on Sep. 3, 2012, both of which are expressly incorporated by reference herein.

INTRODUCTION

The present invention relates to certain compounds capable of forming metal-organic frameworks (MOFs), particularly MOFs which selectively sorb one component (e.g. para-xylene) from a mixture of components (e.g. m-/p-xylene mixture). The invention also relates to methods of producing and using said compounds.

BACKGROUND

There is a widespread demand for high purity xylenes, and therefore a need for effective, practical and cost effective methods of manufacturing the same. High purity mixed xylenes are used as a solvents in chemical manufacturing, agricultural sprays, adhesives, paints, and coatings. Xylene is also an ingredient in aviation fuel and gasoline, and is used as a feedstock material in the chemical, plastic, and synthetic fibre industries. Isomers of xylene are used in manufacturing various polymers. As feedstocks, o-xylene is used in making phthalic anhydride (PA); m-xylene for isophthalic acid; and p-xylene is used exclusively for making dimethyl terephthalate and terephthalic acid (DMT/TPA) which are raw materials used in the manufacture of polyethylene terephthalate (PET) used in polyester fibers, molded plastics, films, and blown beverage bottles4.

The separation of high purity p-xylene from a mixture of mixed xylenes—m-xylene, o-xylene, p-xylene and ethylbenzene—is currently performed by one of the following methods: (1) crystallisation, (2) adsorption, or (3) a hybrid crystallisation/adsorption process5. Distillation is not used due to the boiling point difference of only 2° C. between p-xylene and ethylbenzene resulting in columns with high reflux ratios and a large number of trays.

Crystallisation-based processes exploit the large freezing point difference between p-xylene and the remaining components in the mixture. The recovery value of p-xylene is limited to the eutectic point, i.e. the temperature at which a second component starts to crystallize. Typical values for recovery are between 60-65 wt % for feed streams with about 20 wt % of p-xylene6. This limitation is one of the main drawbacks of crystallisation when processing feeds with a low concentration of p-xylene7. Furthermore, low temperature crystallisation methods have other serious drawbacks, including the large amount of energy required for cooling, and the heat-transfer problems that arise as solid p-xylene coats the inner walls of a cooled crystallisation vessel.

The more recent trend has been to design hybrid processes involving a first stage based on adsorption and a second stage based on crystallisation. Often, zeolites are used as adsorbents in the separation of xylene isomers, but zeolites have their own drawbacks, since they require very specific operating conditions, such as optimal hydration levels, in order to ensure peak performance.

More recently, alternative adsorbents have been developed 1' 2' 3' 7' 9'[10]. For instance, UOP LLC have developed metal-organic frameworks (MOFs) as adsorbents for xylene. US 20110420779 describes the use of the MOFs Cr-MIL-101 and Al-MIL-53 as adsorbents for adsorbing para-xylene, and Zn-MOF-5 for ortho-xylene, in their widely used simulated moving bed technology. However, the adsorption selectivity of MOFs of the prior art, particularly when used to purify xylene mixtures, is sometimes inadequate or inconsistent.

An object of the present invention is to provide alternative compounds to serve as MOFs.

A further object of the present invention is to provide alternative MOFs for purifying xylene mixtures.

A further object of the present invention is to provide MOFs with improved sorption selectivity, especially with respect to xylene mixtures.

A further object of the present invention is to provide an improved method of purifying mixtures, such as xylene mixtures.

SUMMARY OF THE INVENTION

According to a first aspect of the present invention, there is provided a compound comprising:
an f-block metal ion (M); and
a polydentate ligand (LIG) able to co-ordinate with M to provide a metal organic framework (MOF) structure;
wherein the LIG group is defined by Formula A (or a suitable ionised form thereof):

CORE-[-L-R]$_n$ (Formula A)

wherein:
n is an integer between 1 and 6 such that n individual and independently defined -L_R groups (i.e. $L_1$-$R_1$ ... $L_n$-$R_n$) are attached to CORE;
CORE comprises one or more aromatic or heteroaromatic systems;
each L group is the same or different, each being independently either absent or a linker selected from the group including (1-3C)alkylene, (2-3C)alkenylene, (2-3C)alkynylene, O, S, SO, $SO_2$, N(R'$_a$), CO, CH(OR'$_a$), CON(R'$_a$), N(R'$_a$)CO, N(R'$_a$)CON (R'$_a$), $SO_2$N(R'$_a$), N(R'$_a$)$SO_2$, OC(R'$_a$)$_2$, SC(R'$_a$)$_2$ and N(R'$_a$)C(R'$_b$)$_2$, wherein R'$_a$ and R$_b$ are each independently hydrogen or (1-8C)alkyl;
each R group is the same or different, each being independently selected from an aryl or heteroaryl group bearing a lone pair of electrons capable of coordinating with M or substituted by a group bearing a lone pair of electrons capable of coordinating with M;
wherein CORE or any R group is optionally further substituted by one or groups selected from halogeno, trifluoromethyl, trifluoromethoxy, cyano, isocyano, nitro, hydroxy, mercapto, amino, formyl, carboxy (incl. carboxylic acid), carbamoyl, ureido, sulphonyl (incl. sulphonic acid), phosphoryl (incl. phosphonic acid), (1-8C)alkyl, (2-8C)alkenyl, (2-8C)alkynyl, (1-8C)alkoxy, (2-8C)alkenyloxy, (2-8C)alkynyloxy, (1-8C)alkylthio, (1-8C)alkylsulphinyl, (1-8C)alkylsulphonyl, (1-8C)alkylamino, di-[(1-8C)alkyl]amino, (1-8C)alkoxycarbonyl, N-(1-8C)alkylcarbamoyl, N,N-di-[(1-8C)alkyl]carbamoyl, (2-8C)alkanoyl, (2-8C)alkanoyloxy, (2-8C)alkanoylamino, N-(1-8C)alkyl-(2-8C)alkanoylamino, (3-6C)alkenoylamino, N-(1-6C)alkyl-(3-6C)alkenoylamino, (3-6C)alkynoylamino, N-(1-6C)

alkyl-(3-6C)alkynoylamino, N'-(1-6C)alkylureido, N',N'-di-[(1-6C)alkyl]ureido, N-(1-6C)alkylureido, N,N'-di-[(1-6C)alkyl]ureido, N,N',N'-tri-[(1-6C)alkyl]ureido, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino;
or an (acceptable) salt and/or solvate thereof.

According to a second aspect of the present invention, there is provided a metal-organic framework (MOF) comprising a compound of the first aspect.

According to a third aspect of the present invention, there is provided a sorbent material comprising the metal-organic framework (MOF) of the second aspect.

According to a fourth aspect of the present invention, there is provided a method of manufacturing a compound of the first aspect, comprising associating an f-block metal ion (M) with a polydentate ligand (LIG), as defined herein, capable of co-ordinating with M to provide a metal organic framework (MOF) structure.

According to a fifth aspect of the present invention, there is provided a method of manufacturing an MOF of the second aspect, comprising providing the compound of the first aspect in a solid form.

According to a sixth aspect of the present invention, there is provided a method of manufacturing a sorbent material of the third aspect, comprising providing a MOF of the second aspect optionally in admixture with one or more auxiliary sorbent substances and/or one or more carrier substances.

According to a seventh aspect of the present invention, there is provided a method of selectively sorbing a desired component from a mixture of components, the method comprising contacting the mixture of components with a sorbent material of the third aspect to selectively sorb the desired component within/to the sorbent material.

According to an eighth aspect of the present invention, there is provided a method of separating a desired component from a mixture of components, the method comprising:
selectively sorbing a desired component from a mixture of components in accordance with the method of the seventh aspect to produce an sorption complex (i.e. comprising the desired component sorbed into/to the sorbent material);
removing any non-sorbed component(s) from contact with the sorption complex; and
optionally recovering the desired component from the sorption complex.

According to a ninth aspect of the present invention, there is provided a purified product comprising (or consisting of) the desired component obtainable by, obtained by, or directly obtained by the method of the eighth aspect.

According to a tenth aspect of the present invention, there is provided a method of separating a p-xylene from a mixture of xylenes, the method comprising:
selectively sorbing p-xylene from a mixture xylenes by contacting the mixture of xylenes with an sorbent material of the third aspect to selectively sorb p-xylene within the sorbent material to produce a sorption complex between the sorbent material and p-xylene;
removing any non-sorbed xylenes from contact with the sorption complex;
optionally recovering the p-xylene from the sorption complex.

According to an eleventh aspect of the present invention, there is provided p-xylene obtainable by, obtained by, or directly obtained by the method of the eighth aspect.

According to a twelfth aspect of the present invention, there is provided a use of the compound of the first aspect, the MOF of the second aspect, or the sorbent material of the third aspect for separating a desired component (e.g. p-xylene) from a mixture of components (e.g. mixture of xylenes).

According to a thirteenth aspect of the present invention, there is provided a method of enriching a mixture, initially comprising a desired component and a non-desired component, in the non-desired component (relative to the desired component), the method comprising:
i) selectively sorbing a desired component from the mixture by contacting the mixture with a sorbent material of the third aspect to selectively sorb the desired component within/to the sorbent material to produce a sorption complex (i.e. comprising the desired component sorbed into/to the sorbent material) and an non-desired-component-enriched mixture;
ii) separating the non-desired-component-enriched mixture from the sorption complex;
iii) optionally repeating step i) upon the non-desired-component-enriched mixture of step ii);
iv) optionally isolating the non-desired component;
v) optionally recovering the desired component from the sorption complex(es).

According to a fourteenth aspect of the present invention, there is provided a purified product comprising (or consisting of) the non-desired component obtainable by, obtained by, or directly obtained by the method of the thirteenth aspect.

According to a fifteenth aspect of the present invention, there is provided a method of separating a m-xylene from a mixture of xylenes comprising p-xylene and m-xylene, the method comprising:
i) selectively sorbing p-xylene from the mixture by contacting the mixture with a sorbent material of the third aspect to selectively sorb the p-xylene within/to the sorbent material to produce a sorption complex (i.e. comprising p-xylene sorbed into/to the sorbent material) and a m-xylene-enriched mixture;
ii) separating the m-xylene-enriched mixture from the sorption complex;
iii) optionally repeating step i) upon the m-xylene-enriched mixture of step ii);
iv) optionally isolating m-xylene from the m-xylene-enriched mixture;
v) optionally recovering p-xylene from the sorption complex(es).

According to a sixteenth aspect of the present invention, there is provided m-xylene obtainable by, obtained by, or directly obtained by the method of the fifteenth aspect.

Features, including optional, suitable, and preferred features of any particular aspect of the present invention are, unless otherwise stated, also features, including optional, suitable, and preferred features of any other aspect of the present invention.

BRIEF DESCRIPTION OF THE DRAWINGS

For a better understanding of the present invention, and to show how embodiments of the same are put into effect, reference is now made, by way of example, to the following figures, in which.

DETAILED DESCRIPTION OF THE INVENTION

Definitions

Figure 1:
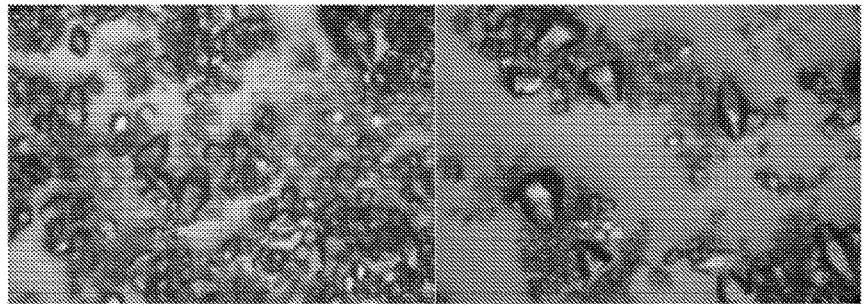
FIG. 1 shows two optical microscope images of Compound 1 at 11.25× magnification.

Herein, the term "metal-organic framework (MOF)" is well known in the art, and generally refers to crystalline compounds in which metal ions (or clusters thereof) are coordinated to (substantially) rigid organic molecules. Typically, MOFs of the present invention form porous structures. Typically the MOFs of the invention are 3-dimensional structures.

Herein the terms "sorb", "sorption", "sorbent", "sorbate" refer to the process of sorption of certain compounds (sorbates) within/to the pores of a particular solid structure (sorbent), such as where an "sorbent material" sorbs a desired component from a component mixture. These terms "sorb", "sorption", "sorbent", "sorbate" encompass "absorb", "absorption" "absorbent", and "absorbate", where sorbates are sorbed within the bulk of a sorbent. Moreover, "sorb", "sorption", "sorbent", "sorbate" also encompasses "adsorb", "adsorption", "adsorbent", and "adsorbate" where sorbates are sorbed to the surface of a sorbent. In some embodiments, the term "sorption" means "absorption". In some embodiments, the term "sorption" means "adsorption".

Herein the term "selectively sorb" refers to a process in which a sorbent (i.e. porous solid material) uptakes one sorbate in preference to other components or potential sorbates which are a part of the same original mixture.

Herein the term "mixture of components" generally refers to a mixture of different compounds from which one particular component is to be preferentially separated, e.g. through sorption into/to a sorbent material.

Herein the term "desired component" refers to a particular component of a mixture intended for selective extraction.

Herein the term "f-block metal ion" is a term of art which refers to the ionised form of a metal residing in the "f-block" of the periodic table of elements. The f-block consists of lanthanides (La-Yb) and actinides (Ac—No), and ions of all such metals are encompassed by the term "f-block metal ion".

Herein the term "polydentate ligand" refers to ligands comprising two or more atoms capable of binding a central f-block metal ion in a coordination complex. This is in contrast to monodentate ligands where only one atom can coordinate (e.g. as per solvents such as $H_2O$ or EtOH).

Herein, where an amount of a component is given as a weight percentage (wt %), unless otherwise stated, this refers to its weight percentage relative to the total weight of the material (or molecule) of which the component forms a constituent part.

In this specification the term "alkyl" includes both straight and branched chain alkyl groups. References to individual alkyl groups such as "propyl" are specific for the straight chain version only and references to individual branched chain alkyl groups such as "isopropyl" are specific for the branched chain version only. For example, "(1-6C)alkyl" includes (1-4C)alkyl, (1-3C)alkyl, propyl, isopropyl and t-butyl. A similar convention applies to other radicals, for example "phenyl(1-6C)alkyl" includes phenyl(1-4C)alkyl, benzyl, 1-phenylethyl and 2-phenylethyl.

The term "(m-nC)" or "(m-nC) group" used alone or as a prefix, refers to any group having m to n carbon atoms.

An "alkylene," "alkenylene," or "alkynylene" group is an alkyl, alkenyl, or alkynyl group that is positioned between and serves to connect two other chemical groups. Thus, "(1-6C)alkylene" means a linear saturated divalent hydrocarbon radical of one to six carbon atoms or a branched saturated divalent hydrocarbon radical of three to six carbon atoms, for example, methylene, ethylene, propylene, 2-methylpropylene, pentylene, and the like.

"(2-6C)alkenylene" means a linear divalent hydrocarbon radical of two to six carbon atoms or a branched divalent hydrocarbon radical of three to six carbon atoms, containing at least one double bond, for example, as in ethenylene, 2,4-pentadienylene, and the like.

"(2-6C)alkynylene" means a linear divalent hydrocarbon radical of two to six carbon atoms or a branched divalent hydrocarbon radical of three to six carbon atoms, containing at least one triple bond, for example, as in ethynylene, propynylene, and butynylene and the like.

"(3-8C)cycloalkyl" means a hydrocarbon ring containing from 3 to 8 carbon atoms, for example, cyclopropyl, cyclobutyl, cyclopentyl, cyclohexyl, cycloheptyl or bicyclo [2.2.1]heptyl.

"(3-8C)cycloalkenyl" means a hydrocarbon ring containing at least one double bond, for example, cyclobutenyl, cyclopentenyl, cyclohexenyl or cycloheptenyl, such as 3-cyclohexen-1-yl, or cyclooctenyl.

"(3-8C)cycloalkyl-(1-6C)alkylene" means a (3-8C)cycloalkyl group covalently attached to a (1-6C)alkylene group, both of which are defined herein.

The term "halo" or "halogeno" refers to fluoro, chloro, bromo and iodo.

The term "heterocyclyl", "heterocyclic" or "heterocycle" means a non-aromatic saturated or partially saturated monocyclic, fused, bridged, or spiro bicyclic heterocyclic ring system(s). The term heterocyclyl includes both monovalent species and divalent species. Monocyclic heterocyclic rings contain from about 3 to 12 (suitably from 3 to 7) ring atoms, with from 1 to 5 (suitably 1, 2 or 3) heteroatoms selected from nitrogen, oxygen or sulfur in the ring. Bicyclic heterocycles contain from 7 to 17 member atoms, suitably 7 to 12 member atoms, in the ring. Bicyclic heterocycles contain from about 7 to about 17 ring atoms, suitably from 7 to 12 ring atoms. Bicyclic heterocyclic(s) rings may be fused, spiro, or bridged ring systems. Examples of heterocyclic groups include cyclic ethers such as oxiranyl, oxetanyl, tetrahydrofuranyl, dioxanyl, and substituted cyclic ethers. Heterocycles containing nitrogen include, for example, azetidinyl, pyrrolidinyl, piperidinyl, piperazinyl, tetrahydrotriazinyl, tetrahydropyrazolyl, and the like. Typical sulfur containing heterocycles include tetrahydrothienyl, dihydro-1,3-dithiol, tetrahydro-2H-thiopyran, and hexahydrothiepine. Other heterocycles include dihydro-oxathiolyl, tetrahydro-oxazolyl, tetrahydro-oxadiazolyl, tetrahydrodioxazolyl, tetrahydro-oxathiazolyl, hexahydrotriazinyl, tetrahydro-oxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or SO2 groups are also included. Examples include the sulfoxide and sulfone forms of tetrahydrothienyl and thiomorpholinyl such as tetrahydrothiene 1,1-dioxide and thiomorpholinyl 1,1-dioxide. A suitable value for a heterocyclyl group which bears 1 or 2 oxo (=O) or thioxo (=S) substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. However, reference herein to piperidino or morpholino refers to a piperidin-1-yl or morpholin-4-yl ring that is linked via the ring nitrogen.

By "bridged ring systems" is meant ring systems in which two rings share more than two atoms, see for example Advanced Organic Chemistry, by Jerry March, 4th Edition, Wiley Interscience, pages 131-133, 1992. Examples of bridged heterocyclyl ring systems include, aza-bicyclo[2.2.1]heptane, 2-oxa-5-azabicyclo[2.2.1]heptane, aza-bicyclo[2.2.2]octane, aza-bicyclo[3.2.1]octane and quinuclidine.

"Heterocyclyl(1-6C)alkyl" means a heterocyclyl group covalently attached to a (1-6C)alkylene group, both of which are defined herein.

The term "heteroaryl" or "heteroaromatic" means an aromatic mono-, bi-, or polycyclic ring incorporating one or more (for example 1-4, particularly 1, 2 or 3) heteroatoms selected from nitrogen, oxygen or sulfur. The term heteroaryl includes both monovalent species and divalent species. Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3-b]furanyl, 2H-furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl. "Heteroaryl" also covers partially aromatic bi- or polycyclic ring systems wherein at least one ring is an aromatic ring and one or more of the other ring(s) is a non-aromatic, saturated or partially saturated ring, provided at least one ring contains one or more heteroatoms selected from nitrogen, oxygen or sulfur. Examples of partially aromatic heteroaryl groups include for example, tetrahydroisoquinolinyl, tetrahydroquinolinyl, 2-oxo-1,2,3,4-tetrahydroquinolinyl, dihydrobenzthienyl, dihydrobenzfuranyl, 2,3-dihydro-benzo[1,4]dioxinyl, benzo[1,3]dioxolyl, 2,2-dioxo-1,3-dihydro-2-benzothienyl, 4,5,6,7-tetrahydrobenzofuranyl, indolinyl, 1,2,3,4-tetrahydro-1,8-naphthyridinyl, 1,2,3,4-tetrahydro-pyrido[2,3-b]pyrazinyl and 3,4-dihydro-2H-pyrido[3,2-b][1,4]oxazinyl Examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered heteroaryl groups include but are not limited to pyridyl, pyrazinyl, pyridazinyl, pyrimidinyl and triazinyl.

A bicyclic heteroaryl group may be, for example, a group selected from:
  a benzene ring fused to a 5- or 6-membered ring containing 1, 2 or 3 ring heteroatoms;
  a pyridine ring fused to a 5- or 6-membered ring containing 1, 2 or 3 ring heteroatoms;
  a pyrimidine ring fused to a 5- or 6-membered ring containing 1 or 2 ring heteroatoms;
  a pyrrole ring fused to a 5- or 6-membered ring containing 1, 2 or 3 ring heteroatoms;
  a pyrazole ring fused to a 5- or 6-membered ring containing 1 or 2 ring heteroatoms;
  a pyrazine ring fused to a 5- or 6-membered ring containing 1 or 2 ring heteroatoms;
  an imidazole ring fused to a 5- or 6-membered ring containing 1 or 2 ring heteroatoms;
  an oxazole ring fused to a 5- or 6-membered ring containing 1 or 2 ring heteroatoms;

an isoxazole ring fused to a 5- or 6-membered ring containing 1 or 2 ring heteroatoms;
a thiazole ring fused to a 5- or 6-membered ring containing 1 or 2 ring heteroatoms;
an isothiazole ring fused to a 5- or 6-membered ring containing 1 or 2 ring heteroatoms;
a thiophene ring fused to a 5- or 6-membered ring containing 1, 2 or 3 ring heteroatoms;
a furan ring fused to a 5- or 6-membered ring containing 1, 2 or 3 ring heteroatoms;
a cyclohexyl ring fused to a 5- or 6-membered heteroaromatic ring containing 1, 2 or 3 ring heteroatoms; and
a cyclopentyl ring fused to a 5- or 6-membered heteroaromatic ring containing 1, 2 or 3 ring heteroatoms.

Particular examples of bicyclic heteroaryl groups containing a six membered ring fused to a five membered ring include but are not limited to benzfuranyl, benzthiophenyl, benzimidazolyl, benzoxazolyl, benzisoxazolyl, benzthiazolyl, benzisothiazolyl, isobenzofuranyl, indolyl, isoindolyl, indolizinyl, indolinyl, isoindolinyl, purinyl (e.g., adeninyl, guaninyl), indazolyl, benzodioxolyl and pyrazolopyridinyl groups.

Particular examples of bicyclic heteroaryl groups containing two fused six membered rings include but are not limited to quinolinyl, isoquinolinyl, chromanyl, thiochromanyl, chromenyl, isochromenyl, chromanyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

"Heteroaryl(1-6C)alkyl" means a heteroaryl group covalently attached to a (1-6C)alkylene group, both of which are defined herein. Examples of heteroaralkyl groups include pyridin-3-ylmethyl, 3-(benzofuran-2-yl)propyl, and the like.

The term "aryl" or "aromatic" means a cyclic or polycyclic aromatic ring having from 5 to 16 carbon atoms. The term aryl includes both monovalent species and divalent species. Examples of aryl groups include, but are not limited to, phenyl, biphenyl, naphthyl and the like. In particular embodiment, an aryl is phenyl.

The term "aryl(1-6C)alkyl" means an aryl group covalently attached to a (1-6C)alkylene group, both of which are defined herein. Examples of aryl-(1-6C)alkyl groups include benzyl, phenylethyl, and the like This specification also makes use of several composite terms to describe groups comprising more than one functionality. Such terms will be understood by a person skilled in the art. For example heterocyclyl(m-nC)alkyl comprises (m-nC)alkyl substituted by heterocyclyl.

The term "optionally substituted" refers to either groups, structures, or molecules that are substituted and those that are not substituted.

Where optional substituents are chosen from "one or more" groups it is to be understood that this definition includes all substituents being chosen from one of the specified groups or the substituents being chosen from two or more of the specified groups.

The phrase "compound of the invention" means those compounds which are disclosed herein, both generically and specifically. Such compounds may include acceptable salts or solvates thereof. Furthermore, a compound defined by a formula (e.g. $[M]_x[LIG]_y$) suitably includes compounds comprising species or units of said formula, optionally in association with further species or units. However, in some embodiments said formula defines the compound precisely, such that said compound consists of species or units of said formula (i.e. where said compound is substantially free of further species or units).

General Methodology and Advantages of the Invention

The present invention provides a new class of MOFs for selectively extracting and separating particular desired components from mixtures. These MOFs are particularly effective at selectively extracting/separating p-xylene from xylene mixtures, though the inherent flexibility of the MOFs of the invention widens the scope of their applicability.

By contacting a MOF of the invention (or sorbent materials formed therefrom) with a liquid mixture, one or more components (preferably one) will be selectively extracted over others in the mixture. This process yields a solid-phase sorption complex comprising the MOF and the extracted component(s), and also "mother liquors" enriched in the remaining non-extracted components. The solid-phase sorption complex can then be separated from the mother liquors before then treating the sorption complex to recover the sorbed component(s) (i.e. sorbates) from the MOF (i.e. sorbent). In this manner, a desired component can be separated from a mixture, whilst the mixture is itself enriched in any remaining components.

Though the MOFs of the invention are considered effective without the need for multiple sorption/separation cycles, it is envisaged that established "simulated moving bed" technology[11,12] known in the art could be employed to make optimum use of the MOFs of the invention.

Advantageously, the MOFs of the present invention offer excellent sorption selectivity, especially with respect to the selective sorption of p-xylene from xylene mixtures. MOFs of the present invention generally outperform MOFs and Zeolites of the prior art in terms of substrate sorption selectivity.

A further advantage of MOFs of the present invention is that they remain efficient and selective over a range of solvation states.

A further advantage of MOFs of the present invention is that they permit liquid phase extractions, particularly with respect to xylenes, thus avoiding problematic handling of solid phase components.

A further advantage of MOFs of the present invention is that they allow for straightforward recovery of substrates sorbed therein/thereto.

A further advantage of MOFs of the present invention is that they can generally be successively re-used in sorption/extraction processes.

Furthermore, the MOFs of the present invention are highly stable on storage, and can withstand aggressive manufacturing conditions, such as high-temperature drying steps. Moreover, the MOFs of the present invention are substantially stable in the presence of moisture and liquid water, which can be crucial in their practical applications.

It has been observed, by way of crystallography, that the MOF structures of the present invention are highly flexible. Without wishing to be found by any particular theory, it appears that the MOFs of the present invention change structure as a desired component is sorbed thereinto/thereto. It is thought that the greater selectivity afforded by MOFs of the present invention is at least in part due to this inherent flexibility, which seemingly allows the MOFs to adopt lower energy structural configurations as they selectively sorb the desired component. This additional energetic factor may account for the increased discrimination for particular components over others in a mixture.

Finally, the discovery of a class of MOFs exhibiting such surprising levels of structural flexibility significantly widens the scope of compound mixtures which may be purified using MOFs. For instance, by varying the ligand and/or metal ion, the MOF can be tuned to selectively sorb a range of different substrates from various different mixtures. As such, the class of MOFs of the present invention are more widely applicable and customisable than any MOFs previously discovered.

Compounds

According to a first aspect of the present invention, there is provided a compound as defined herein.

M and LIG are suitably respectively present in the compound in a molar ratio of x:y. x and y suitably respectively indicate the relative stoichiometries of M and LIG within the compound, both x and y being greater than zero.

The compounds of the present invention are suitably MOF-compounds, i.e. capable of adopting an MOF structure in a crystalline form. The crystal structure of the MOF-compounds of the invention is readily determined by methods known in the art such as crystallography.

In a particular embodiment, the present invention provides an MOF-compound defined by Formula I:

$[M]_x[LIG]_y$ (Formula I)

wherein:
M is an f-block metal ion;
LIG is a polydentate ligand as defined herein;
x and y indicate the relative stoichiometries of M and LIG respectively, both x and y being greater than zero;
or an (acceptable) salt and/or solvate thereof.

The compounds of the invention essentially comprise a metal-ligand complex. Suitably the polydentate ligands (LIG) are co-ordinated to some or all of the metal ions (M) present in the complex. In a particular embodiment, the MOF-compound comprises a complex in which the f-block metal ion has a co-ordination number of at least 6, suitably 9 (as discernable by crystallography). The co-ordination denticity may vary for each metal-ligand combination, and individual ligands may in some cases bridge between metal ions. The metal-ligand complex is suitably neutral.

Though the metal ions (M) and polydentate ligand (LIG) suitably constitute the majority (i.e. over 50%) of the molecular weight of the MOF-compounds, other species, such as solvates and/or auxiliary counterions (whether counterions to the metal ions or counterions to the ligand), may also be present in the complexes.

The MOF-compound may be provided as a salt thereof. For instance, where the metal-ligand complex is positively charged (e.g. if there are insufficient negatively charged polydentate ligand species within the complex to neutralise the positively charged metal ions), the MOF-compound may be provided as a salt with an appropriate anion (e.g. a halide). Alternatively, where the metal-ligand complex is negatively charged (e.g. if the negative charges of the ligands outnumber the positive charges of the metal ions), the MOF-compound may be provided as a salt with an appropriate cation (e.g. a metal ion, whether an f-block metal or otherwise). In a particular embodiment, the MOF-compound is (substantially) neutral, i.e. the ligand charges balance with the metal ion charges.

In a particular embodiment, the respective oxidation (or ionisation) states of M and LIG are of (substantially) equal magnitude but opposite polarity, most suitably 3+ and 3- respectively. As such, x and y may be substantially equal and the metal-ligand complex substantially neutral.

The MOF-compound may be provided as a solvate thereof. In such circumstances, the solvate suitably includes solvent molecules co-ordinated directly to the metal ions (M). Alternatively the MOF-compound may be (substantially) free of solvate.

The presence of solvates may affect the structure of the MOFs, but will not generally affect the relative stoichiometry between the metal ions (M) and the polydentate ligands (LIG), assuming said solvate is uncharged.

The presence of auxiliary counterions (e.g. halides, such as chloride) may, however, affect the relative stoichiometry between the metal ions (M) and the polydentate ligands (LIG). This may depend on whether such auxiliary counterions are associated with the outer sphere of the complex or inner co-ordination sphere (i.e. directly co-ordinated with the meal ions). Auxiliary counterions may be those present in the original species used to form the MOF-compounds.

Stoichiometry

The relative stoichiometry of the metal ion (M) to polydentate ligand (LIG) depends on a number of factors, including the relative amounts of metal ions and polydentate ligand used to form the MOF-compounds, the oxidation state of the metal ions, the ionisation state of the ligand, the presence of auxiliary counterions, the presence of solvates.

M and LIG are suitably respectively present in the compound in a molar ratio of x:y. As such, the compound may be said to comprise species defined by the formula $[M]_x[LIG]_y$, where x and y respectively indicate the relative stoichiometries of M and LIG within the compound, both x and y being greater than zero.

In some embodiments, the MOF-compound may be polydentate ligand-deficient, i.e. so that the co-ordination spheres of the metal ions are unsaturated with respect to the ligand. On the other hand, in other embodiments, the MOF-compound may be over-saturated with polydentate ligand, for instance, such that more ligands are involved in bridging between the metal ions. In other embodiments, the MOF-compounds are somewhere between these two extremes. The proportions of metal ions to ligand may affect the structure and/or pore sizes of the MOFs formed from the MOF-compounds.

The ratio of metal ion (M) to polydentate ligand (LIG) is expressed as x:y or x/y. As mentioned above, this ratio, which reflects the relative stoichiometry between the metal ions (M) and polydentate ligand (LIG), may vary depending on a number of factors, and may in some embodiments be predetermined for optimum effect. Suitably the ratio x:y is between 10:1 and 1:10, suitably between 5:1 and 1:5, more suitably between 2:1 and 1:2, and most suitably substantially 1:1. Suitably the x/y ratio is such that the total charge of metal ions is at least 70% neutralised by the total charge of the polydentate ligand, more suitably at least 90% neutralised, most suitably at least 95% neutralised. Any charge on the metal ions not neutralised by the polydentate ligand is suitably neutralised by auxiliary ligands or counterions. In a particular embodiment, the total charge of the metal ions is (substantially) 100% neutralised by the charge of the polydentate ligand.

In some embodiments, the MOF-compounds of the invention comprise a plurality of different ligands and/or auxiliary counterions.

The MOF-compound may comprise multiple different polydentate ligands, as defined herein. For instance, the LIG group may in fact consist of multiple different LIG groups each independently defined as herein described in relation to the LIG group. As such, the LIG group may be represented as $[LIG_1]_{y1}[LIG_2]_{y2} \ldots [LIG_n]_{yn}$ such that the MOF-compound is defined by the Formula $[M]_x[LIG_1]_{y1}[LIG_2]_{y2} \ldots [LIG_n]_{yn}$. In such embodiments, y is the sum of the individual ligand stoichiometries, i.e. $y=y1+y2+\ldots+yn$. The MOF-compound may comprise other auxiliary ligands, such as monodentate ligands and the like. In this manner, the MOF-complex may be considered "doped", so as to affect the structure and/or pore sizes to provide the optimal MOF for a given circumstance.

Likewise, the MOF-compounds of the invention may also comprise a plurality of different metal ions, so long as at least one f-block metal ion (M) is present. Suitably at least 10 wt % of the total metal ions present in the MOF-compound are f-block metal ions, suitably at least 50 wt %, more suitably at least 90 wt %, most suitably at least 95 wt %. In a particular embodiment, all of the metal ions present in the MOF-compound are f-block metal ions.

F-Block Metal Ions

M is an f-block metal ion, i.e. from the "f-block" of the periodic table of elements.

In a particular embodiment, the f-block metal ion (M) is a lanthanide metal ion. As such, the f-block metal ion is suitably selected from a lanthanum, cerium, praseodymium, neodymium, promethium, samarium, europium, gadolinium, terbium, dysprosium, holmium, erbium, thulium, ytterbium, lutetium, or yttrium ion. In a particular embodiment the f-block metal ion is selected from a lanthanum, cerium, praseodymium, neodymium, samarium, or europium ion. In a particular embodiment the f-block metal ion is selected from a lanthanum, cerium, praseodymium, neodymium, or samarium ion. In a particular embodiment, the f-block metal ion is a cerium ion. In a particular embodiment, the f-block metal ion is selected from a lanthanum, cerium, praseodymium, neodymium or samarium ion In a particular embodiment, the f-block metal ion is neodymium.

The f-block metal ion is suitably cationic, and suitably has an oxidation state of 2+, 3+, or 4+. In a particular embodiment, the f-block metal ion is in the 3+ oxidation state.

In a particular embodiment, the f-block metal ion is cerium (III)—i.e. $Ce^{3+}$. In a particular embodiment, the f-block metal ion is neodymium (III)—i.e. $Nd^{3+}$.

Ligand

The polydentate ligand (LIG) is able to co-ordinate with M to provide a metal organic framework (MOF) structure. As such, LIG comprises co-ordinating functionalities, i.e. functional groups with a lone pair of electrons capable of coordinating with M.

In some embodiments, the LIG group may include a plurality of different LIG groups. As such, LIG may be represented as $[LIG_1]_{y1}[LIG_2]_{y2} \ldots [LIG_n]_{yn}$.

The or each LIG group is defined by Formula A (or a suitable ionised form thereof):

CORE—[-L-R]$_n$ (Formula A)

wherein:
n is an integer between 1 and 6 such that n individual and independently defined -L_R groups (i.e. $L_1$-$R_1$ . . . $L_n$-$R_n$) are attached to CORE;
CORE comprises one or more aromatic or heteroaromatic systems;
each L group is the same or different, each being independently either absent or a linker selected from the group including (1-3C)alkylene, (2-3C)alkenylene, (2-3C)alkynylene, O, S, SO, $SO_2$, N(R'$_a$), CO, CH(OR'$_a$), CON(R'$_a$), N(R'$_a$)CO, N(R'$_a$)CON(R'$_a$), $SO_2$N(R'$_a$), N(R'$_a$)$SO_2$, OC(R'$_a$)$_2$, SC(R'$_a$)$_2$ and N(R'$_a$)C(R'$_b$)$_2$, wherein R'$_a$ and R'$_b$ are each independently hydrogen or (1-8C)alkyl;
each R group is the same or different, each being independently selected from an aryl or heteroaryl group bearing a lone pair of electrons capable of coordinating with M or substituted by a group bearing a lone pair of electrons capable of coordinating with M;

wherein CORE or any R group is optionally further substituted by one or groups selected from halogeno, trifluoromethyl, trifluoromethoxy, cyano, isocyano, nitro, hydroxy, mercapto, amino, formyl, carboxy (incl. carboxylic acid), carbamoyl, ureido, sulphonyl (incl. sulphonic acid), phosphoryl (incl. phosphonic acid), (1-8C)alkyl, (2-8C)alkenyl, (2-8C)alkynyl, (1-8C)alkoxy, (2-8C)alkenyloxy, (2-8C)alkynyloxy, (1-8C)alkylthio, (1-8C)alkylsulphinyl, (1-8C)alkylsulphonyl, (1-8C)alkylamino, di-[(1-8C)alkyl]amino, (1-8C)alkoxycarbonyl, N-(1-8C)alkylcarbamoyl, N,N-di-[(1-8C)alkyl]carbamoyl, (2-8C)alkanoyl, (2-8C)alkanoyloxy, (2-8C)alkanoylamino, N-(1-8C)alkyl-(2-8C)alkanoylamino, (3-6C)alkenoylamino, N-(1-6C)alkyl-(3-6C)alkenoylamino, (3-6C)alkynoylamino, N-(1-6C)alkyl-(3-6C)alkynoylamino, N'-(1-6C)alkylureido, N',N'-di-[(1-6C)alkyl]ureido, N-(1-6C)alkylureido, N,N'-di-[(1-6C)alkyl]ureido, N,N',N'-tri-[(1-6C)alkyl]ureido, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino.

Any definitions herein regarding the LIG group may suitably encompass any acceptable ionised forms thereof. For instance, references to LIG group substituents such as carboxylic acids may also include its conjugate base, i.e. a carboxylate anion.

The polydentate ligand suitably complexes directly with the f-block metal ion (i.e. within the inner co-ordination sphere).

The polydentate ligand (LIG) may be a neutral species, for instance, where auxiliary counterions serve to neutralise the charge of the f-block metal ions. However, in preferred embodiments LIG comprises one or more ionised groups to thereby provide one or more anions. Such anions may then serve as counterions to the f-block metal ions as well as well as co-ordinating groups within the metal-ligand complex. In a particular embodiment, LIG comprises one or more ionised groups characterised as the conjugate base of an acid (e.g. carboxylate groups).

In certain embodiments, LIG comprises either or both ionised and/or ionisable groups (e.g. carboxylate and carboxylic acid groups). Suitably the ratio of ionised to ionisable groups can be selectively varied, for instance, by varying pH. The ratio of ionised to ionisable groups within LIG may be adapted so as to provide a (substantially) neutral metal-ligand complex. For instance, LIG may comprise 4 co-ordinating groups, 3 of which are ionised (e.g. carboxylate) and 1 of which is a non-ionised ionisable group (e.g. carboxylic acid) so as to give an overall 3– charge capable of neutralising a 3+ charge on the f-block metal ion.

Suitably, LIG comprises 4 or more ionised and/or ionisable groups. Suitably, LIG comprises 4 or more carboxylic and/or carboxylate groups. Suitably, LIG comprises 4 carboxylic and/or carboxylate groups.

The CORE group of the ligand suitable has n individual and independently defined -L_R groups attached directly to appropriate position(s) of the aromatic and/or heteroaromatic systems, preferably at different positions where n is greater than 1. Suitably the -L-R groups are juxtaposed around the CORE group to enable polydentate co-ordination with M, and optionally also bridging between M units.

Particular LIG groups suitable in the MOF-compounds of the invention include, for example, compounds of the formula A, or suitably ionised forms thereof, wherein, unless otherwise stated, each of CORE, n, L groups, and R groups has any of the meanings defined hereinbefore or in any of paragraphs (1) to (23) hereinafter:—

(1) n is an integer between 2 and 4.

(2) n is 4 such that 4 individual and independently defined -L_R groups (i.e. $L_1$-$R_1$, $L_2$-$R_2$, $L_3$-$R_3$, $L_4$-$R_4$) are attached to CORE.

(3) CORE comprises one or more aromatic systems, optionally substituted as herein defined.

(4) CORE is an aromatic system defined by any one of:

optionally substituted as herein defined.

(5) CORE is a benzene ring, optionally substituted as herein defined.

(6) CORE is a benzene ring and n is 4 such that the benzene ring is substituted in the 1, 2, 4, and 5-positions with 4-L_R groups (i.e. $L_1$-$R_1$, $L_2$-$R_2$, $L_3$-$R_3$, $L_4$-$R_4$) as herein defined, wherein the benzene ring is optionally further substituted as herein defined.

(7) each L group is the same or different, each being independently either absent or a (2-3C)alkynylene linker.

(8) All L groups are the same.

(9) One or more L groups are absent.

(10) All L groups are absent.

(11) each R group is the same or different, each being independently selected from an aryl group substituted by a group bearing a lone pair of electrons capable of coordinating with M, wherein each R group is optionally further substituted as herein defined.

(12) each R group is the same.

(13) each R group is aryl substituted by a group bearing a lone pair of electrons capable of coordinating with M selected from:

cyano, nitro, hydroxy, amino, formyl, carboxy (incl. carboxylic acid), carbamoyl, ureido, sulphonyl (incl. sulphonic acid), phosphoryl (incl. phosphonic acid), (1-8C)alkoxy, (2-8C)alkenyloxy, (2-8C)alkynyloxy, 1-8C)alkylamino, di-[(1-8C)alkyl]amino, (1-8C)alkoxycarbonyl, N-(1-8C)alkylcarbamoyl, N,N-di-[(1-8C)alkyl]carbamoyl, (2-8C)alkanoyl, (2-8C)alkanoyloxy, (2-8C)alkanoylamino, N-(1-8C)alkyl-(2-8C)alkanoylamino, (3-6C)alkenoylamino, N-(1-6C)alkyl-(3-6C)alkenoylamino, (3-6C)alkynoylamino, N-(1-6C)alkyl-(3-6C)alkynoylamino, N'-(1-6C)alkylureido, N',N'-di-[(1-6C)alkyl]ureido, N-(1-6C)alkylureido, N,N'-di-[(1-6C)alkyl]ureido, N,N',N'-tri-[(1-6C)alkyl]ureido, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino;

wherein each R group is optionally further substituted as herein defined.

(14) Each R group is defined by:

wherein at least one of $Z_1$, $Z_2$, $Z_3$, $Z_4$, and $Z_5$ is a group bearing a lone pair of electrons capable of coordinating with M as defined herein, whilst the others of $Z_1$, $Z_2$, $Z_3$, $Z_4$, and $Z_5$ are each independently hydrogen or any optional substituent defined herein in relation to an R group.

(15) each R group is aryl substituted by a carboxy (incl. carboxylic acid) group, wherein each R group is optionally further substituted as herein defined.

(16) each R group is aryl substituted by a carboxylate or carboxylic acid group, wherein each R group is optionally further substituted as herein defined.

(17) CORE or any R group is optionally further substituted by one or more groups selected from halogeno, cyano, amino, carboxy (incl. carboxylic acid), carbamoyl, (1-8C)alkyl, (1-8C)alkoxy, (1-8C)alkylsulphonyl, (1-8C)alkylamino, di-[(1-8C)alkyl]amino, (1-8C)alkoxycarbonyl, (2-8C)alkanoyloxy, (2-8C)alkanoylamino, N-(1-8C)alkyl-(2-8C)alkanoylamino, (3-6C)alkenoylamino, N-(1-6C)alkyl-(3-6C)alkenoylamino.

(18) CORE or any R group is optionally further substituted by one or more groups selected from halogeno, cyano, amino, carboxy (incl. carboxylic acid), carbamoyl, (1-4C)alkyl, (1-4C)alkoxy, (1-4C)alkylsulphonyl, (1-4C)alkylamino, di-[(1-4C)alkyl]amino, (1-4C)alkoxycarbonyl, (2-4C)alkanoyloxy, (2-4C)alkanoylamino, N-(1-4C)alkyl-(2-4C)alkanoylamino, (3-4C)alkenoylamino, N-(1-4C)alkyl-(3-4C)alkenoylamino.

(19) CORE or any R group is optionally further substituted by one or more groups selected from halogeno, cyano, amino, carboxy (incl. carboxylic acid), (1-4C)alkyl, (1-4C)alkoxy, (1-4C)alkylsulphonyl, (1-4C)alkylamino, di-[(1-4C)alkyl]amino, (1-4C)alkoxycarbonyl, (2-4C)alkanoylamino.

(20) CORE or any R group is optionally further substituted by one or more groups selected from fluoro, chloro, bromo, iodo, methyl, (1-8C)alkyl, amino, (1-8C)alkylamino, di-[(1-8C)alkyl]amino, (2-8C)alkanoylamino, carboxy (incl. carboxylic acid, carboxylate, or carboxy ester), hydroxyl, (1-8C)alkoxy, (1-4C)alkylsulphonyl, or cyano.

(21) CORE is free of optional further substituents.

(22) Optional further substituents for any of the R groups may themselves be a group (as defined herein) bearing a lone pair of electrons capable of coordinating with M.

(23) All R groups are free of optional further substituents.

In a particular embodiment, the LIG group is defined by Formula B (or a suitable ionised form thereof), optionally further substituted as defined herein:

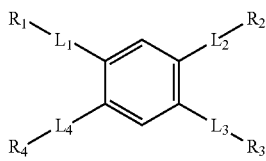
(Formula B)

where the L and R groups (i.e. $L_1$, $L_2$, $L_3$, $L_4$, and $R_1$, $R_2$, $R_3$, $R_4$) are as defined herein.

In a particular embodiment, the LIG group is defined by Formula C (or a suitable ionised form thereof), optionally further substituted as defined herein:

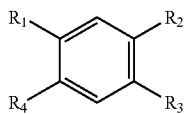
(Formula C)

where the R groups ($R_1$, $R_2$, $R_3$, $R_4$) are as defined herein.

In a particular embodiment, the LIG group is defined by Formula D (or a suitable ionised form thereof), optionally further substituted as defined herein:

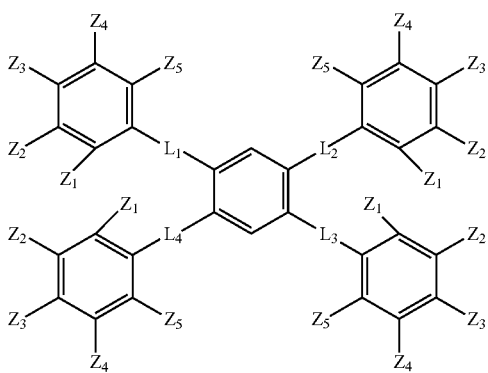
(Formula D)

wherein $L_1$, $L_2$, $L_3$, and $L_4$ are each independently defined as herein, and wherein at least one of $Z_1$, $Z_2$, $Z_3$, $Z_4$, and $Z_5$ is a group bearing a lone pair of electrons capable of coordinating with M as defined herein, whilst the others of $Z_1$, $Z_2$, $Z_3$, $Z_4$, and $Z_5$ are each independently hydrogen or any optional substituent defined herein in relation to R group. In a particular embodiment, $Z_1$ and $Z_5$ are hydrogen. In another embodiment, $Z_1$, $Z_3$, and $Z_5$ are hydrogen whilst $Z_2$ and $Z_4$ are groups other than hydrogen as defined herein (most suitably both are carboxylate or carboxylic acid groups). In another embodiment, $Z_1$, $Z_2$, $Z_4$, and $Z_5$ are hydrogen whilst $Z_3$ is a group other than hydrogen as defined herein (most suitably a carboxylate or a carboxylic acid group).

In a particular embodiment, the LIG group is defined by Formula E (or a suitable ionised form thereof), optionally further substituted as defined herein:

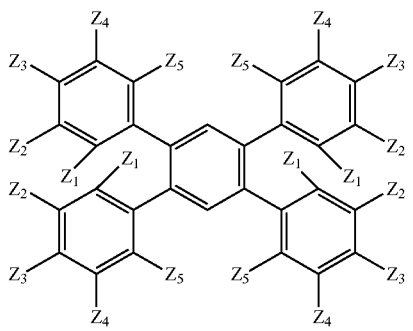
(Formula E)

wherein at least one of $Z_1$, $Z_2$, $Z_3$, $Z_4$, and $Z_5$ is a group bearing a lone pair of electrons capable of coordinating with M as defined herein, whilst the others of $Z_1$, $Z_2$, $Z_3$, $Z_4$, and $Z_5$ are each independently hydrogen or any optional substituent defined herein in relation to R group. In a particular embodiment, $Z_1$ and 4 are hydrogen. In another embodiment, $Z_1$, $Z_3$, and $Z_5$ are hydrogen whilst $Z_2$ and $Z_4$ are groups other than hydrogen as defined herein (most suitably both are carboxylate or carboxylic acid groups). In another embodiment, $Z_1$, $Z_2$, $Z_4$, and $Z_5$ are hydrogen whilst $Z_3$ is a group other than hydrogen as defined herein (most suitably a carboxylate or a carboxylic acid group).

In a particular embodiment, the LIG group is selected from any one of (or a suitable ionised form of):

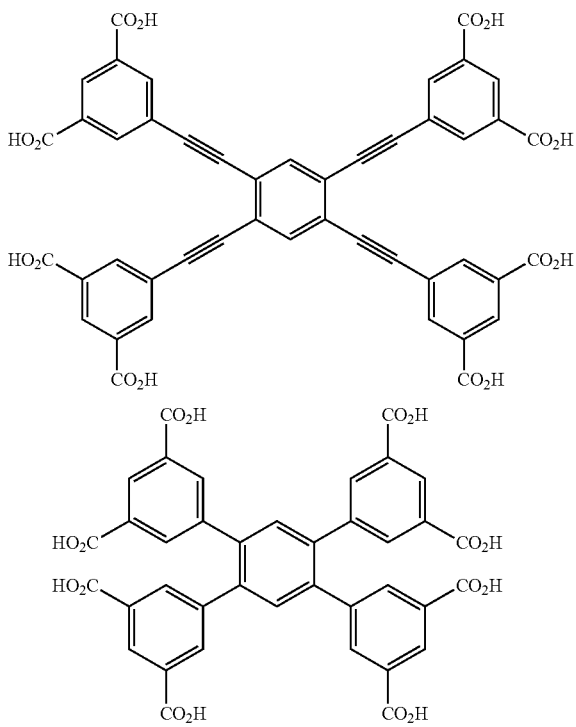

-continued

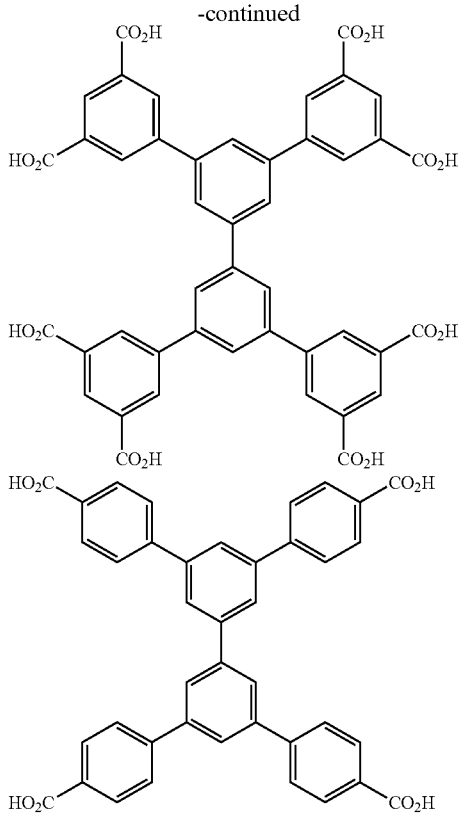

optionally further substituted as defined herein.

In a particular embodiment, the LIG group is (or a suitable ionised form of):

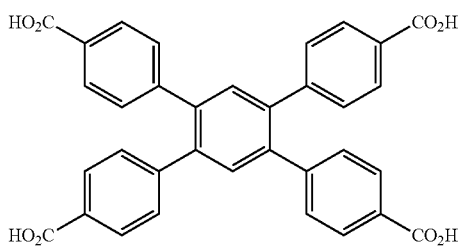 [SMILES: O=C(O)c1ccc(-c2cc(-c3ccc(C(=O)O)cc3)c(-c3ccc(C(=O)O)cc3)cc2-c2ccc(C(=O)O)cc2)cc1]

optionally further substituted as defined herein. Such LIG groups are known as 4',5'-bis(4-carboxyphenyl)-[1,1':2',1''-terphenyl]-4,4''-dicarboxylic acids, and are otherwise known in the art as tetrakis(4-carboxyphenyl)benzene ($H_4$TCPB or HTCPB).

In a particular embodiment, the LIG group is:

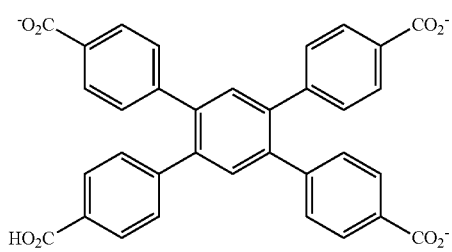

optionally further substituted as defined herein.

Solvates

Solvated forms of the MOF-compounds defined herein also fall within the ambit of the present invention. This includes solvates in the outer coordination sphere as well as within the inner co-ordination sphere (e.g. directly complexed to the f-block metal).

The MOF-compounds may comprise one or more solvates. Solvates may include any suitable solvating molecules, though most typically one or more of the solvate has a lone pair of electrons capable of co-ordinating with M. As such, the solvates typically comprise a hetero atom, such as nitrogen or oxygen. Suitably the solvates are protic solvents, such as water or alcohols. In an embodiment, the solvates are water and/or ethanol. In a particular embodiment, the solvates are both water and ethanol.

Typical solvates include $[M]_x[LIG]_y \cdot (EtOH)_a(H_2O)_b$, where x and y are between 0.1 and 1, a is a number between 0 and 0.5 (suitably 0.1 and 0.3) and b is a number between 0 and 3 (suitably between 1 and 2.8) In a particular embodiment, especially where M is cerium(III), LIG is HTCPB, and x and y are substantially equal to 1, the solvate is either $[M]_x[LIG]_y(H_2O)_{2.75}(EtOH)_{0.28}$, $[M]_x[LIG]_y$. or $[M]_x[LIG]_y(H_2O)_{1.8}$.

In a particular embodiment, the MOF-compound comprises less than 20 wt % solvate(s), suitably less than 10 wt %, suitably less than 5 wt %, suitably less than 2 wt %. In a particular embodiment, the MOF-compound is (substantially) free of solvate(s).

The solvation state typically affects the 3-dimensional structure of the MOF, particularly the pore sizes and/or the size and/or shape of channels to the pores. In general, the less solvate present in the MOF or MOF-compound, the more selectively the MOF can sorb p-xylene from a mixture of xylenes. However, MOFs of the present invention may be tuned appropriately.

Metal-Organic Frameworks (MOFs)

The present invention provides a metal-organic framework (MOF) comprising a compound as defined herein. The MOF per se generally relates to the isolated solid form the MOF-compound. MOFs of the present invention are generally porous, and suitably comprise pores and/or channels into which or through which substrates may be sorbed (whether absorbed or adsorbed). The class of MOFs of the present invention are particularly effective at selectively sorbing one component from a component mixture, especially p-xylene from a mixture of xylenes. This is due to the favourable pore/channel structure exhibited, which allows for discrimination between components of a mixture.

Though references herein to an MOF per se relates to the isolated solid form the MOF-compound, features described herein in relation to the MOF-compound (e.g. solvates and solvate content) may equally apply to the MOF per se.

In a particular embodiment, the MOF is (substantially) free of solvates.

Suitably, the MOF is a porous material in which at least some of the pores are accessible to the xylenes (i.e. not occupied by other guests). This is generally the "active" form of the MOF.

Suitably the MOFs of the present invention are substantially physically composed of porous crystalline material, and substantially free of amorphous and/or non-porous material. The physical 3-D structure is suitably determined by powder X-ray diffraction and/or scanning electron microscopy. The MOFs are suitably composed of porous crystalline material within the limits of these techniques. i.e. >99%.

The MOFs of the present invention are suitably provided in crystalline form, suitably as a powder.

Sorbent Materials

The present invention provides a sorbent material comprising the metal-organic framework (MOF) as defined herein.

The sorbent material may be absorbant, adsorbent, or both. In a particular embodiment, the sorbent material is absorbent.

The sorbent material may be provided in a variety of solid physical forms. Most suitably the sorbent material is provided as a powder, most suitably a crystalline powder. The sorbent material is suitably provided as a mobile solid form, for instance, so that it may be used in association with "simulated moving bed" technology.

The sorbent material may comprise the MOF of the invention in admixture with one or more further MOFs of the present invention and/or one or more auxiliary sorbent substances and optionally one or more carrier substances. Further MOFs may include other MOFs falling within the scope of the invention, or other MOFs of the prior art. Auxiliary sorbent substances may include a range of substances known in the art, such as zeolites.

The inclusion of additional MOFs or auxiliary sorbent substances, may increase selectivity or the overall efficiency of the sorption process.

The inclusion of addition carrier substances may improve the practical handling of the sorbent materials. Suitably any carrier substances used within the sorbent materials are inert, at least in relation to the mixtures upon which the sorbent materials are intended to be used.

In a particular embodiment, the sorbent material comprises at least 70 wt % MOF of the invention, suitably at least 80%, suitably at least 95%. In a particular embodiment, the sorbent material consists of the MOF of the present invention.

Method of Manufacturing the Compounds of the Invention

The present invention provides a method of manufacturing a compound of the first aspect, comprising associating an f-block metal ion (M) with a polydentate ligand (LIG), as defined herein. Suitably, the method involves reacting a salt of the f-block metal ion (M) with a polydentate ligand (LIG), or suitable ionised form thereof. In some embodiments the salt of the f-block metal ion (M) is reacted with the polydentate ligand (LIG) (or a suitable ionised form thereof) with M in a stoichiometric excess of at least 1.5:1, suitably at least 1.8:1, suitably at least 2:1, suitably to ensure that most or all of the ligand reacts. In an embodiment, the f-block metal ion (M) and the polydentate ligand (LIG) are associated in the required stoichiometric proportions to yield a compound comprising species defined by the formula $[M]_x[LIG]_y$. In a particular embodiment, the method comprises solvothermal combination of an f-block metal ion (M) salt with the polydentate ligand (LIG). Solvothermal syntheses are well known in the art. Solvothermal combination suitably involves heating the ingredients together in the presence of an organic solvent (suitably an alcohol, e.g. ethanol) optionally in the presence of water. Solvothermal combination suitably involves heating at a temperature between 70 and 150° C., suitably between 110 and 130° C. under pressure such that at least some of the solvent is still liquid or supercritical fluid under the reaction conditions.

The method suitably comprises reacting a salt of the f-block metal ion (M) with a polydentate ligand (LIG) in a solvent system. The solvent system may comprise one or more solvents. The solvent system may comprise two or more solvents, most suitably two solvents.

Suitably, at least one of the solvents of the solvent system bears a lone pair of electrons capable of co-ordinating with the f-block metal ion (M). Suitably, at least one of the solvents of the solvent system is a protic solvent. The solvent system suitably comprises an alcohol, most suitably ethanol. The solvent system may comprise water.

In a particular embodiment, the solvent system comprises ethanol and water. The ratio of ethanol to water in the solvent system is suitably between 10:1 and 1:10 by volume, suitably between 5:1 and 1:5 by volume, more suitably between 2:1 and 1:2 by volume, most suitably 1:1 by volume.

The particular solvents and proportions thereof used in the reaction to form the MOF-compounds can have an important influence on the resulting 3-dimensional structure of the MOFs formed. For instance, the presence of water assists the reaction more generally, facilitating solubilisation amongst other things. However, the presence of an alcohol, especially ethanol, was found (especially where the f-block metal ion is cerium(III)) to affect the final crystalline form of the MOF, in some cases mitigating against the formation of amorphous solids.

The method may suitably involve separation of the MOF-compound from the solvent system. This may involve filtration of the MOF from the solvent system. In a particular embodiment, the MOF-compound is isolated directly from the reaction solvent system.

The MOF-compound yielded may initially be a solvate. Such solvates can be important, as explained above, in determining the original 3D-crystal structure before solvates are optionally subsequently removed.

The method may optionally involve an additional recrystallisation step, for instance, to furnish the correct MOF-solvate in the first instance.

The method may also involve a drying and/or desolvation step. Suitably desolvation involves exposing the resulting MOF-compound to a temperature of 70° C. or greater for a period of time suitable to obtain the desired form of the MOF-compound (whether partially desolvated or completely desolvated). Suitably desolvation involves exposure of the MOF-compound to temperatures of 95° C. or greater, more suitably 150° C. or greater, most suitably 250° C. greater, for period of time suitable to attain the desired level of desolvation.

Samples of the MOF-compound may be taken during the desolvation process and analysed (e.g. using crystallographic techniques) to determine whether or not desolvation should be ceased, for instance, to yield a desired partially desolvated compound.

Generally, with the MOFs of the present invention, complete desolvation was found to irreversibly provide a stable desolvated structure.

An aspect of the present invention provides an MOF-compound obtainable by, obtained by, or directly obtained by the method of manufacturing a compound described herein.

Method of Manufacturing the Compounds of the MOFs of the Invention

The present invention provides a method of manufacturing a MOF, comprising providing the MOF-compound as defined herein in a solid form.

In many embodiments, the MOF is provided directly from the reaction to produce the MOF-compound, suitably directly from the reaction solvent system thereof.

However, the MOF may be further treated and/or purified if deemed necessary. For instance, the MOF may be recrystallised in an appropriate solvent system, optionally the same as the reaction solvent system described hereinbefore. This may furnish the MOF as the appropriate solvate before it is then dried/desolvated as described hereinbefore.

In general, the MOF is completely desolvated before it is used.

Method of Manufacturing the Compounds of the Sorbent Materials of the Invention

The present invention provides a method of manufacturing a sorbent material, comprising providing a MOF as defined herein optionally in admixture with one or more auxiliary sorbent substances and/or one or more carrier substances.

The sorbent material may be merely the MOF itself, and as such is formed merely through the provision of the MOF. However, in some embodiments, the MOF is further mixed with one or more auxiliary sorbent substances and/or one or more carrier substances. For instance, the sorbent material may additionally comprise silica, particularly porous silica. In a particular embodiment, the sorbent material comprises the MOF associated (or attached to) a support, particularly a (porous) silica support. In such circumstances, the MOF may be grown upon the support. In such circumstances, a homogenous mixture is suitably formed through thorough mixing Method of Use of Compounds, MOFs, and Sorbent Materials of the Invention The present invention provides a use of an MOF-compound, an MOF, or an sorbent material as define herein for separating a desired component (e.g. p-xylene) from a mixture of components (e.g. mixture of xylenes).

The present invention provides a method of selectively sorbing a desired component from a mixture of components, the method comprising contacting the mixture of components with a sorbent material to selectively sorb the desired component within/to the sorbent material.

The present invention provides a method of separating a desired component from a mixture of components, the method comprising:
selectively sorbing a desired component from a mixture of components by contacting the mixture of components with a sorbent material to selectively sorb the desired component within/to the sorbent material to produce a sorption complex (i.e. comprising the desired component sorbed into/to the sorbent material); and
removing any non-sorbed components from contact with the sorption complex;
optionally recovering the desired component from the sorption complex.

In a particular aspect of the present invention, there is provided a method of separating a p-xylene from a mixture of xylenes, the method comprising:
selectively sorbing p-xylene from a mixture of xylenes by contacting the mixture of xylenes with an sorbent material to selectively sorb p-xylene within/to the sorbent material to produce a sorption complex between the sorbent material and p-xylene;
removing any non-sorbed xylenes from contact with the sorption complex;
optionally recovering the p-xylene from the sorption complex.

Before use, the sorbent material (or MOF) may be activated, for example, by exposing to heat (e.g. a temperature of at least 70° C., or at least 95° C., or at least 150° C., or at least 250° C.) for sufficient time to desolvate.

In a particular embodiment, the MOF is selected from Ce(HTCPB), Ce(HTCPB)(H$_2$O)$_{2.75}$(ETOH)$_{0.28}$ Ce(HTCPB)(H$_2$O)$_{2.75}$(EtOH)$_{0.28}$, Ce(HTCPB)(H$_2$O)$_{1.8}$, which are suitably used to separate p-xylene (the desired component) from a mixture of xylenes (suitably a mixture of p-/m-xylene at least).

Substrate Mixture and the Desired Component

The mixture from which a desired component is sorbed is suitably a liquid mixture at standard ambient temperature and pressure (SATP), i.e. 25° C. and 100 kPa. Suitably the desired component is itself a liquid at SATP.

In some embodiments the liquid mixture is a solution of the desired component. However, in preferred embodiments, the mixture is (substantially) free from solvents (especially solvents with a boiling point less than 100° C.).

The mixture from which a desired component is sorbed is suitably a mixture of two or more components, i.e. a mixture of the desired component and at least one other component, suitably at least one other similar component.

In an embodiment, the mixture comprises the desired component and at least one other component which is an isomer of the desired component. Suitably the isomers are structural isomers (as opposed to stereoisomers).

In another embodiment, the mixture comprises the desired component and at least one other component which is structurally identical to the desired component, save for a different degree of saturation (i.e. the desired component may be unsaturated and the at least one other component saturated, and vice versa).

In a particular embodiment, the mixture comprises an aromatic desired component and at least one other aromatic component. In a particular embodiment, the mixture comprises two or more benzene derivatives, suitably two or more different (1-8C)dialkylbenzenes, one of which is the desired component.

In a particular embodiment, the mixture comprises p-xylene and m-xylene. Suitably p-xylene is the desired component. The mixture may additionally comprise other structural isomers of p-xylene.

In another embodiment, the mixture comprises propane and propene, one of which is the desired component.

Selective Sorption

Sorption may include absorptions (within the bulk) and/or adsorption (at the surface). In a particular embodiment, sorption is (predominantly) absorption.

Selectively sorbing the desired component from the mixture of components involves contacting the mixture with a sorbent material for suitable time to allow the desired component to be selectively sorbed within/to the sorbent material.

Contacting the mixture with the sorbent material may involve eluting the sorbent material with the mixture (e.g. such as in column chromatography). In this manner, the sorbent material is a stationary phase, whilst the mixture is a mobile phase. In a particular embodiment, the mixture is contact with a simulated moving bed of sorbent material and eluted accordingly.

Alternatively, contacting may involve simple mixing of the mixture and sorbent material, optionally under agitate conditions. In a particular embodiment, there is no agitation.

Suitably, the relative loadings of sorbent material (particularly the total amount of MOF) and the mixture of components (particularly the desired component) are selected for optimal sorption selectivity. Such selectivity can be established by running a number of experiments at different loadings and examining the composition of sorbed product to determine which loading combination provides the optimal selectivity. In an embodiment, the relative loadings are calculated with reference to the proportion of MOF in the sorbent material and the proportion of desired component in the substrate mixture.

Suitably, during the contacting step, the weight ratio between the sorbent material and the mixture is from 1:100 to 100:1, suitably 1:30 to 10:1, suitably 1:20 to 1:1. In a particular embodiment the weight ratio between the sorbent material and the mixture is between 1:10 and 1:9.

Suitably, during the contacting step, the weight ratio between the MOF in the sorbent material and the desired component in the mixture is from 1:50 to 50:1, suitably 1:15 to 5:1, suitably 1:10 to 2:1. In a particular embodiment the weight ratio between the sorbent material and the mixture is between 1:5 and 1:4.

Contact time is suitably at least 30 second, suitably at least 1 minute, more suitably at least 10 minutes, and optionally at least 24 hours. Contact time is suitably less than 14 days, suitably less than 8 days, and may be less than 48 hours.

Separating Sorption Complex from Mother Liquors

The sorption complex is a complex between the desired component and the sorbent material, especially the MOFs contained therein. The mother liquors remaining following sorption of the desired component may be separated from the sorption complex by methods well known in the art regarding separating solids from liquids. In a particular embodiment the method of separation comprises a form of filtration. Where the contacting step essentially involves eluting the sorbent material (stationary phase) with the mixture (mobile phase), the mother liquors may be simply allowed to drain from the sorbent material or otherwise be pumped away from the sorbent material or otherwise removed under suction. This is essentially a form of filtration, since the stationary phase remains in place whilst the liquid exits.

The sorption complex is optionally washed, for example with a suitable solvent (e.g. that dissolves or is miscible with the mother liquors), to remove any excess mother liquors remaining associated with the sorption complex. For instance, where the original mixture is a xylene mixture, dichloromethane or another suitable organic solvent may be used to wash the sorption complex.

The sorption complex may be optionally dried further, for example, through suction drying.

Recovering Sorbate from Sorption Complex

The sorption complex may be further treated to extract the desired component therefrom. Such treatments may involve chemical treatments (e.g. to break down the sorbent material to release the desired component) or physical treatments (e.g. high temperatures).

In a particular embodiment, the sorption complex is chemically treated to break down the MOF (i.e. through disintegrating the 3-dimensional structure of the MOF, for instance, by dissolving the polydentate ligand (LIG)) so as to release the desired component. The desired component is then suitably separated from the broken down MOF and any other components within the sorbent material, to isolate the desired component.

In a particular embodiment, the sorption complex is treated with aqueous base (e.g. aqueous sodium hydroxide) to break down the MOF (e.g. Ce(HTCPB) to release the desired component (e.g. p-xylene). The resulting mixture is the optionally filtered (to remove any superfluous solids) before the desired component is separated from the aqueous phase. Where the desired component is a water-immiscible component such as a xylene, this process is straight forward since xylene and the aqueous phase will be segregated at a phase boundary. Such water-immiscible components can be separated from the aqueous phase, and the aqueous phase optionally further washed with organic solvents to extract more of the desired component from the aqueous layer.

The overall process of separating a desired component from a mixture of components suitably provides a "selectivity" for the desired component over undesired component(s) of greater than 4.5, suitably greater than 4.8. Selectivity is calculated by reference to the relevant GC traces, which produce a peak for pX and mX with a concentration assigned to it, Selectivities ($\alpha$) are calculated from the formula used in the literature—$a_{AB}=(Y_A/Y_B)/(X_A/X_B)$, where $Y_A$ and $Y_B$ are mole fractions of absorbed phase and $X_A$ and $X_9$ are mole fractions of initial phase A and B respectively[13].

Products of the Extraction Process

According to a ninth aspect of the present invention, there is provided a purified product comprising (or consisting of) the desired component obtainable by, obtained by, or directly obtained by the method of the eighth aspect.

According to an eleventh aspect of the present invention, there is provided p-xylene obtainable by, obtained by, or directly obtained by the method of the eighth aspect.

Specific Embodiments

In a particular embodiment, the MOF-compound is defined by:
M being Ce (III);
LIG being $H_4$TCPB (or an ionised form thereof, especially the corresponding tricarboxylate tri-anion);
The ratio x:y being between 0.9:1 and 1.1:1.

In a particular embodiment, the MOF-compound is completely or substantially desolvated.

In a particular embodiment, the MOF-compound is for separating p-xylene from xylene mixtures.

EXAMPLES

Equipment and Materials

Reagents and solvents were purchased from Sigma-Aldrich and used as received without further purification.

PXRD data was either collected in transmission geometry on station 111, Diamond Light Source using synchrotron radiation at a wavelength of 0.825054 Å (synchrotron XRD) or in transmission geometry in a capillary using a Cu Bruker D8 Advance Powder Diffractometer (lab XRD). Samples were rotated to minimise the effect of preferred orientation and hence improve the quality of the data.

Elemental analyses (C and H) were obtained using a Thermo EA1112 Flash CHNS—O Analyzer.

For single crystal XRD, single crystals were mounted in Fomblin inert oil directly from mother liquor on a two stage capillary fibre and transferred to the cold gas stream (100 K) of the Rigaku AFC12 Kappa 3 circle goniometer. Single-crystal diffraction data was collected using a Rigaku Mo-007HF rotating anode source at 0.7107247 Å and Rigaku Saturn724+ (2×2 bin mode). An inefficient full-sphere of data was collected at 1.0° scan widths and 10 second uncorrelated exposure times. The initial unit cell was determined using CrystalClear-SM Expert 2.0 r[14]. The data was processed using FS-Process[15]. Scaling and absorption correction was undertaken using SADABS 2008/4[16]. The final structure was solved using Olex2[17] SHELXS-97 and refined using SHELXL-97[18].

TGA was carried out using a SDT500 analyser using air as the carrier gas.

$CO_2$ and $CH_4$ gas sorption isotherms were measured using the Intelligent Gravimetric Analyser (IGA) from Hiden. As made sample was washed with water and ethanol and left to air dry prior to use. A sample of 1 was outgassed at 100° C. under dynamic vacuum ($10^{-5}$ mbar) until constant mass loss was reached. For the Brunauer-Emmett-Teller (BET) surface area measurement, the sample was cooled to 195 K by means of a Dewar vessel containing dry ice. The isotherm was measured to an absolute $CO_2$ pressure of 1 bar. For measurements at 273 K and 298 K, the sample was cooled using a Dewar vessel containing ice and water and water alone respectively. The samples in these cases were measured to a $CO_2$ pressure of 5 bar.

GC measurements were carried out using a ZB-Wax capillary column. Solutions of 0.1% (w/v) were prepared in DCM for injection into the GC. All separations were carried out using the following conditions: Carrier Gas, 50 KPa He; Column Temp Program, isothermal at 40° C.; Detector, 300° C.; Injector, 250° C.

Example 1—Cerium tetrakis(4-carboxyphenyl)benzene ($H_4TCPB$) Metal Organic Framework

Preparation of tetrakis(4-carboxyphenyl)benzene ($H_4TCPB$) Ligand

The following reaction was run 6 times in parallel using a Radley's Carousel and all 6 reactions were combined for the work-up and isolation:

1, 2, 4, 5-Tetrabromobenzene (3.15 g, 8 mmol), p-tolylboronic acid (6.53 g, 48 mmol) and potassium carbonate (8.85 g, 64 mmol) were charged to a round-bottomed flask followed by toluene (120 mL), methanol (40 mL) and deionised water (32 mL). Nitrogen was bubbled through the reaction mixture for 5 min then tetrakis(triphenylphospine)palladium(0) was charged and the mixture was heated at reflux under a nitrogen atmosphere for 4 days. The 6 biphasic reaction mixtures were cooled to ambient temperature, combined and the layers separated. The organic layer was washed with 1 M HCl (250 mL), water (2×250 mL), dried over $MgSO_4$ and filtered. The filtrate was concentrated on a rotary evaporator until approximately 50 mL of solvent remained. The suspension was diluted with 50 mL of acetone and filtered to afford 16.0 g of crude material. The solid was dissolved in hot toluene, a small amount of insoluble material was removed by filtration and the filtrate was concentrated to a volume of 50 ml. The suspension was allowed to cool to ambient temperature and the solid was collected by filtration. The cake was washed with toluene (10 ml) and dried under vacuum to afford 14.5 g (69% yield) 1, 2, 4, 5-tetra-p-tolyl-benzene as a white solid. $^1H$ NMR ($CDCl_3$): 7.47 (2H, s, Ar—H), 7.12 (8H, d, Ar—H), 7.04 (8H, d, Ar—H), 2.32 (12H, s, 4×$CH_3$). This was then oxidised using a reported oxidation step to yield the final product of 1, 2, 4, 5-tetra(4-carboxyphenyl)-benzene[19].

Preparation of cerium (III) tetrakis(4-carboxyphenyl)benzene ($H_4TCPB$) MOF (Compound 1)

Figure 2:
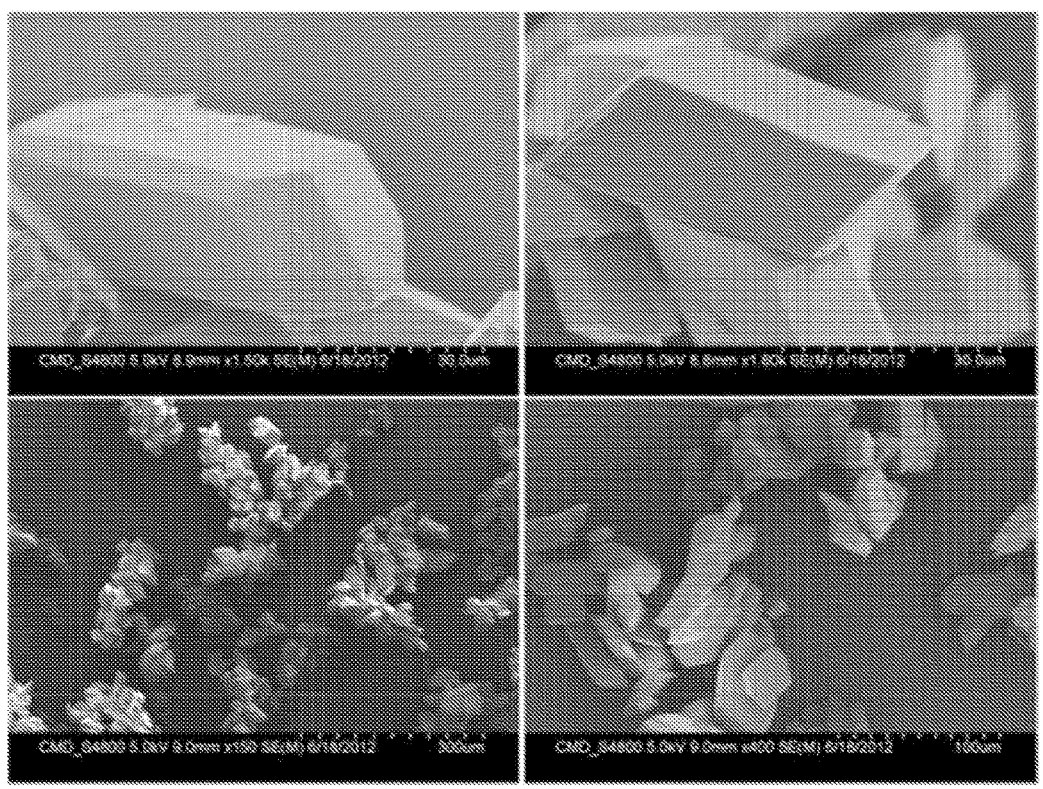
FIG. 2 shows four SEM images of a crystal of Compound 1.

Solvothermal combination of $Ce(NO_3)_3 \cdot 6H_2O$ and $H_4TCPB$ has produced a neutral framework with the formula $Ce(HTCPB)(EtOH)_{0.28}(H_2O)_{2.75}$ (1) in the form of colourless single crystals (FIGS. 1 and 2). FIG. 1 shows two optical microscope images of Compound 1 at 11.25× magnification. FIG. 2 shows four SEM images of crystallites of Compound 1.

In the present example, the solvothermal combination involves $Ce(NO_3)_3 \cdot 6H_2O$ (20 mg) and $H_4TCPB$ (10 mg) added to EtOH (3 mL) and H2O (3 mL) in 12 mL borosilicate glass vial and the vials sealed. Heat at 2° C./min to 120° C. for 48 hours and cooled at 0.2° C./min back down to room temperature (25° C.). At this stage the product was present in the mother liquor in the form of colourless single crystals which were separated from the mother liquor by vacuum filtration and washed with EtOH and $H_2O$ to yield pure compound. Batches were also produced at 3× the scale (3× reagent in 3× solvent in 40 mL glass vial). These scaled-up batches were used in the selectivity tests below.

Compound 1 is activated by heating at 100° C. under vacuum overnight yielding the desolvated Compound 2, which has the formula Ce(HTCPB).

Analytical Data

The phase purity of as grown Compound 1 was confirmed by powder X-ray diffraction (Synchrotron XRD—see FIG. 3), thermogravimetric analysis (TGA—see FIG. 4), and CHN microanalysis (see Table 1).

Figure 3:
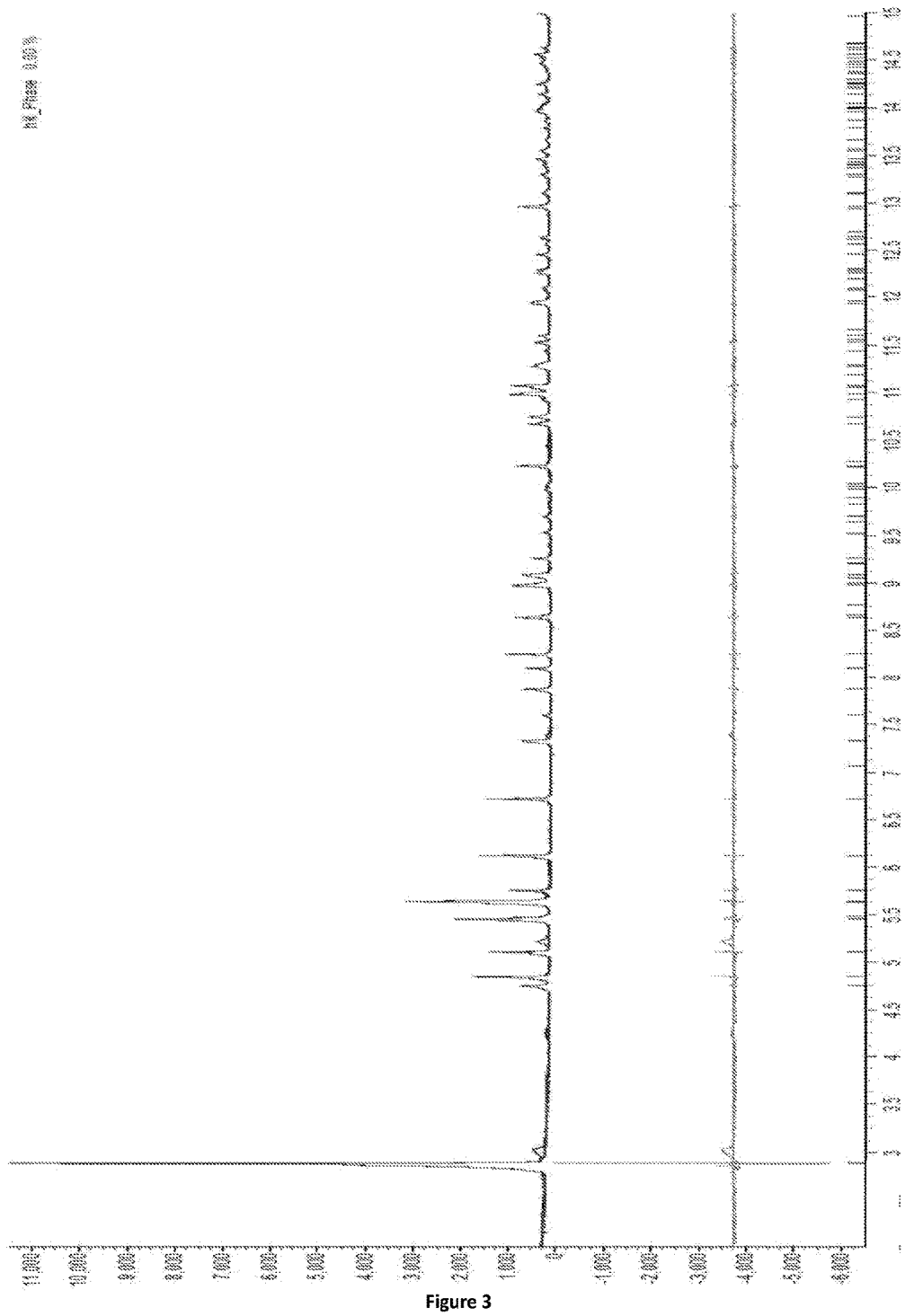
FIG. 3 shows a PXRD profile of Compound 1. Final observed (blue), calculated (red) and difference (grey) X-ray powder diffraction profile measured in transmission geometry with synchrotron radiation of 0.825054 Å using a sealed 0.5 mm capillary for the Le Bail refinement of 1 ($R_{wp}$=11.427%, $R_{exp}$=4.566%, $\chi^2$=2.503; a=10.69480(14), b=10.70195(11), c=16.91349(15) Å, α=76.56960(77), β=83.24766(99), γ=68.83849(91). $P_{-1}$). Reflection positions are marked.

FIG. 3 shows an PXRD profile of Compound 1. Final observed (blue), calculated (red) and difference (grey) X-ray powder diffraction profile measured in transmission geometry with synchrotron radiation of 0.825054 Å using a sealed 0.5 mm capillary for the Le Bail refinement of 1 ($R_{wp}$=11.427%, $R_{exp}$=4.566%, $\chi^2$=2.503; a=10.69480(14), b=10.70195(11), c=16.91349(15) Å, α=76.56960(77), β=83.24766(99), γ=68.83849(91). $P_{-1}$). Reflection positions are marked.

Figure 4:
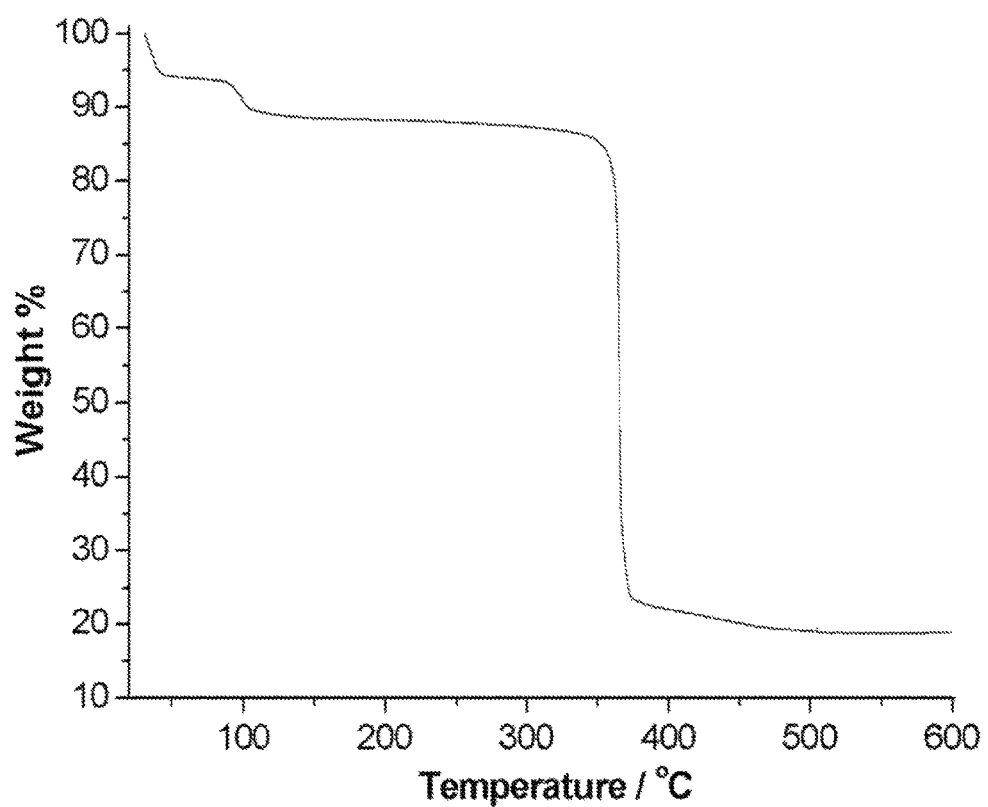
FIG. 4 shows a TGA profile of compound 1.

FIG. 4 shows a TGA profile of compound 1.

TABLE 1

CHN microanalysis of compounds 1 and 2.

| Formula | Theory/% | Found/% | Solvent content from CHN/% | Solvent content from TGA/% | Final $CeO_2$ from CHN/% | Final $CeO_2$ from TGA/% |
|---|---|---|---|---|---|---|
| $Ce(HTCPB)(H_2O)_{2.75}(EtOH)_{0.28}$ (1) | C: 54.76 H: 3.37 | C: 54.76 C: 3.48 | 9.80 | 11.00 | 20.59 | 20.00 |
| Ce(HTCPB) (2) | C: 58.70 H: 2.75 | C: 58.20 H: 2.66 | — | — | — | — |

For 1, the weight change of 11% observed for the loss of the guest and coordinated EtOH and $H_2O$ molecules before reaching a plateau at 120° C. is in good agreement with the values calculated from microanalysis. The final mass percentage of 20.1% corresponds to 1 equivalent of $CeO_2$ after heating at 600° C.

A UV-visible spectrum shows absorption at 260 and 350 nm. Following excitation at 350 nm, 1 displays ligand based fluorescence which is quenched upon coordination to the metal, however no metal to ligand charge transfer is observed.

Structure of Compound 1

Compound 1 is a 3D framework with 1D porosity formed by channels running along the a-axis. The asymmetric unit contains one crystallographically unique Ce(III) ion with a coordination number of 9 and one mono-protonated HTCPB ligand, leaving an overall neutral framework with the formula $Ce(HTCPB)(H_2O)_{2.75}(EtOH)_{0.28}$.

The structure is based on isolated $Ce_2$ dimers which are held in a 3D structure by the HTCPB ligand. Each $Ce_2$ dimer is bridged by two Ce—O—C—O—Ce bidentate bridges and two Ce-$\mu^2$-O—C—O—Ce tridentate bridges, filling five of the nine sites in the coordination sphere of Ce. Two monodentate carboxylates are also coordinated each Ce, one protonated and one non-protonated at the axial positions of the $Ce_2$ dimer. The final two sites in the coordination sphere are filled by coordination of one $H_2O$ and one EtOH atom to each Ce, oriented into the channels. Of the four carboxylate groups belonging to each HTCPB ligand, two coordinate to Ce via monodentate coordination the third coordinates to two Ce via a bidentate carboxylate bridge and the fourth coordinates to two Ce via a bidentate bridge with $\mu_2$-O. This leaves a framework containing $Ce_2$ dimers linked in three dimensions via HTCPB ligands. As mentioned, one of the monodentate carboxylate groups is protonated which can be seen from the asymmetric (Ce—)O17-C16-O18(—H) bond lengths of 1.227 and 1.301 Å respectively in comparison with the more uniform (Ce—)O28-C26-O27 of 1.248 and 1.253 Å seen in the non-protonated carboxylate group. It is expected that C=O will have a shorter bond length than C—O, whereas conjugated C—O bonds will have lengths somewhere intermediate to the C=O and C—O. This is also highlighted in a hydrogen bonded pocket within the structure, in which the protonated and non-protonated carboxylate groups from two separate ligands interact with one another within the 3D structure and also interact with OH of the Ce-coordinated EtOH.

Figure 5:
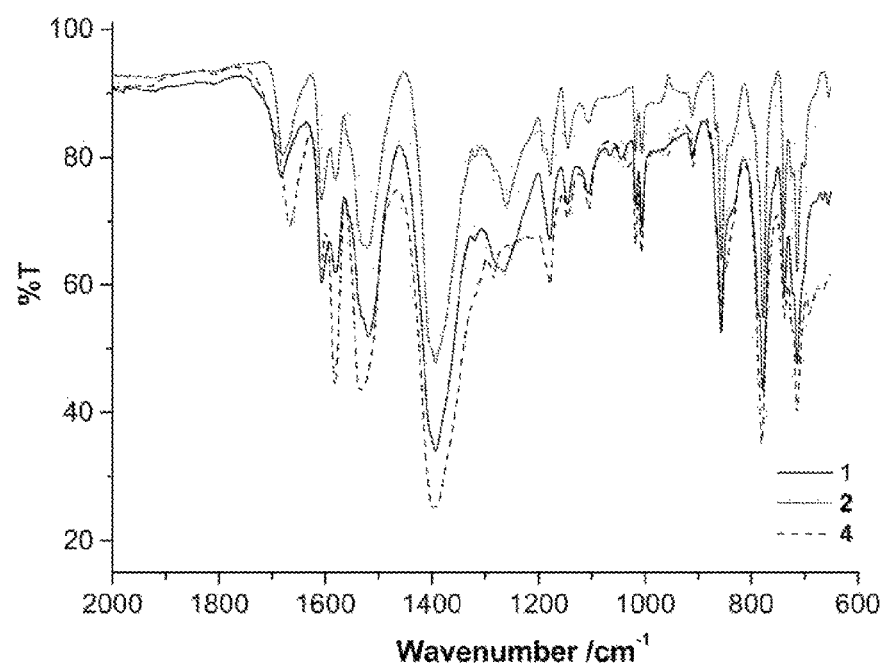
FIG. 5 shows IR spectra of Compounds 1 and 2 showing the presence of C=O carbonyl (1690 cm$^{-1}$), several conjugated C—O environments (1620-1550 cm$^{-1}$) and single C—O bond (1400 cm$^{-1}$), highlighting the presence of a protonated carboxylic acid group within the structure.

FIG. 5 shows IR spectra of Compounds 1 and 2 showing the presence of C=O carbonyl (1690 $cm^{-1}$), several conjugated C—O environments (1620-1550 $cm^{-1}$) and single C—O bond (1400 $cm^{-1}$), highlighting the presence of a protonated carboxylic acid group within the structure.

The IR of 1 (as per FIG. 5) shows that there are three carboxylate bonding environments within the material. Characteristic carboxylate frequencies include C=O carbonyl carboxylate (1684 $cm^{-1}$), conjugated C—O (1607-1521 $cm^{-1}$) and C—O single bond (1258 $cm^{-1}$) which indicates the presence of both protonated (O=C(R)—OH) and non-protonated (conjugated O—C(R)—O$^-$) carboxylate groups within the MOF. The protonated monodentate carboxylate therefore interacts with Ce via the lone pair of the carbonyl oxygen (Ce—O18=C—O17H).

Following the removal of channel solvent and the coordinated $H_2O$ and EtOH molecules in the asymmetric unit, the framework can be penetrated by a spherical probe radius of 1.4 Å, 0.9 Å and 0.5 Å down the a, b and c-axes respectively, with the largest spherical void being 4.4 Å in diameter, giving a packing index of 54.26%. Upon standing at room temperature in air, single crystals of 1 which have been removed from their mother liquor and left on a glass slide for any residual sovent to evaporate over a period of 7 days have been found to be stable in air. Structural analysis of these crystals show that during this time coordinated EtOH has started to exchange with $H_2O$ from the air, however synthesis in pure $H_2O$ yielded an amorphous product, showing both EtOH and $H_2O$ are ideally present for the synthesis of this crystalline MOF.

Structure of Compound 2

Compound 2 is the desolvated form of compound 1, in which both channel solvent and coordinated $H_2O$ and EtOH molecules have been removed from each Ce centre. This allows for the formation of a bidentate carboxylate bridge between the $Ce_2$ dimers forming Ce-carboxylate chains propagating parallel to the c-axis. This change does not affect the dimensionality as it remains a 3D framework, but the carboxylate bridge forming where EtOH and $H_2O$ have been removed from the Ce centres takes overall coordination number down from 9 to 8. The non-coordinated 068 atom of the non-protonated monodentate carboxylate unit coordinated to each Ce bonds to Ce' in the adjacent $Ce_2$ dimer, meaning where there was originally no connecivity between $Ce_2$ in 1, there are now two bidentate carboxylate bridges present; Ce—O67/O67'-C66/C66'-O68/O68'-Ce' (' denotes symmetry generated element). In 2, the framework can be penetrated by a spherical probe radius of 2.1 Å, 0.6 Å and 0.3 Å down the a, b and c-axes respectively, with the largest spherical void being 4.6 Å in diameter with a packing index of 56.17%.

Compound 2 has two distinct channels present. The 'blue' channel is the smaller of the two channels and is square in shape. It lies between the 1-/2- and 4-/5-positions of the central aromatic ring of the HTCPB ligand, with the pendent carboxyphenyl groups leading to Ce lining the channels. The inversion centre in the middle of the channel and within the blue channel, the protonated O17-C16-O18(—H) carboxylate unit is present. The larger 'green' channel lies between the 2-/4- and 5-/1-positions of the same central aromatic ring of the HTCPB ligand. In this case, the carboxyphenyl groups also line the channels, however due to the larger distance between the pendent groups, the channel is more rectangular in shape. The inversion centre again is at the centre of the channel, meaning both channels are symmetrical, but due to their position with respect to the ligand, the blue channel is square and the green is rectangular. (In 1, the channel solvent is coloured depending on the channel name assignments; $H_2O$ is found in the blue channel and EtOH is found in the green channel of 1.

The total solvent accessible volume of 2 is 405 Å$^3$, corresponding to 24.9% of the total volume of the unit cell calculated using Olex2. This can be broken down into the two channels: The blue channel is responsible for 11.4% of this void space with a volume of 186.2 Å$^3$ per unit cell. The green channel accounts for the remaining 13.5% of the void space, with a volume of 218.8 Å$^3$.

Porosity

The porosity of 2 towards $N_2$, $CO_2$, $CH_4$ and $H_2O$ was investigated by collecting full isotherms following activation of 1 using conditions of 100° C. under $10^{-5}$ mbar overnight. In all cases an initial weight loss of 10% was observed with the loss of coordinated and guest EtOH and $H_2O$ to give 2, which is comparable with the solvent loss observed in the TGA data (as per FIG. 4).

Figure 6:
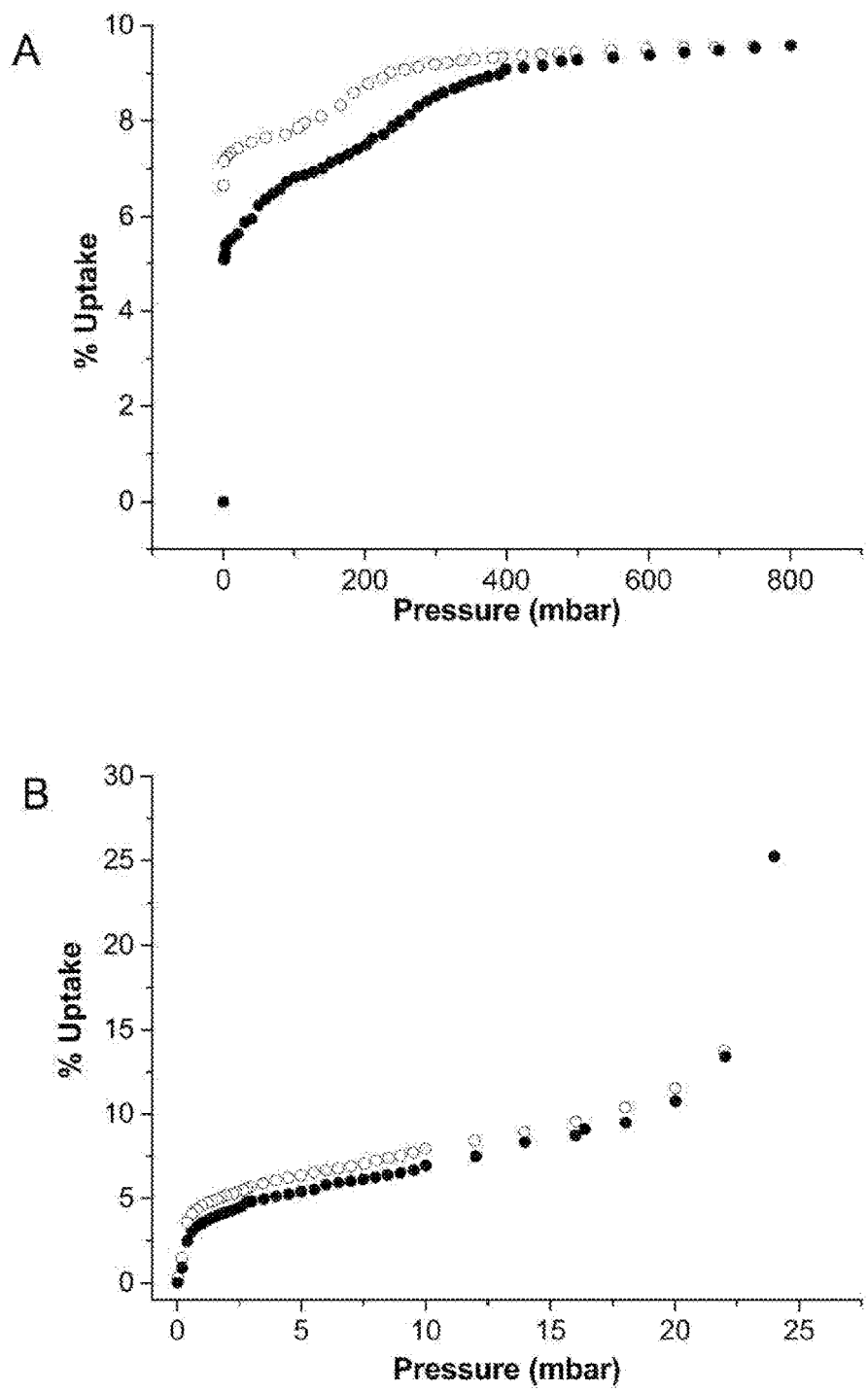
FIG. 6 shows (a) an $N_2$ isotherm of compound 2 collected at 77 K; and (b) an $H_2O$ isotherm of compound 2 collected at 295 K following activation 1 at 100° C. at 10$^{-5}$ mbar overnight.

FIG. 6 shows (a) an $N_2$ isotherm of compound 2 collected at 77 K; and (b) an $H_2O$ isotherm of compound 2 collected at 295 K following activation 1 at 100° C. at $10^{-5}$ mbar overnight.

Figure 7:
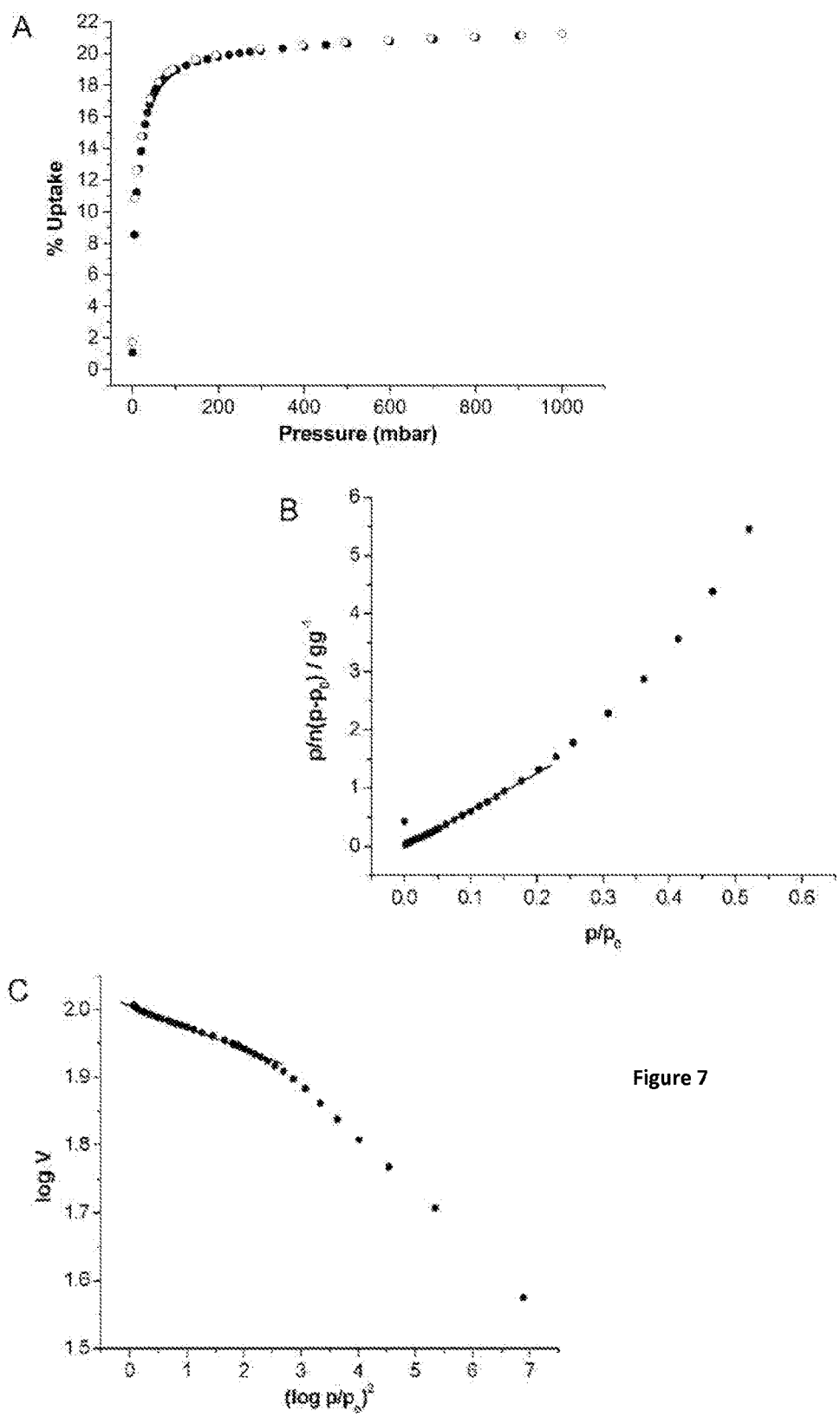
FIG. 7 shows (a) a $CO_2$ isotherm of compound 2 collected at 195 K following activation 1 at 100° C. at 10$^{-5}$ mbar overnight; (b) a BET plot for surface area determination; and (c) a Dubnin-Raduschevich plot for calculation of pore volume based on 195 K isotherm.

FIG. 7 shows (a) a $CO_2$ isotherm of compound 2 collected at 195 K following activation 1 at 100° C. at $10^{-5}$ mbar overnight; (b) a BET plot for surface area determination; and (c) a Dubnin-Raduschevich plot for calculation of pore volume based on 195 K isotherm.

Figure 8:
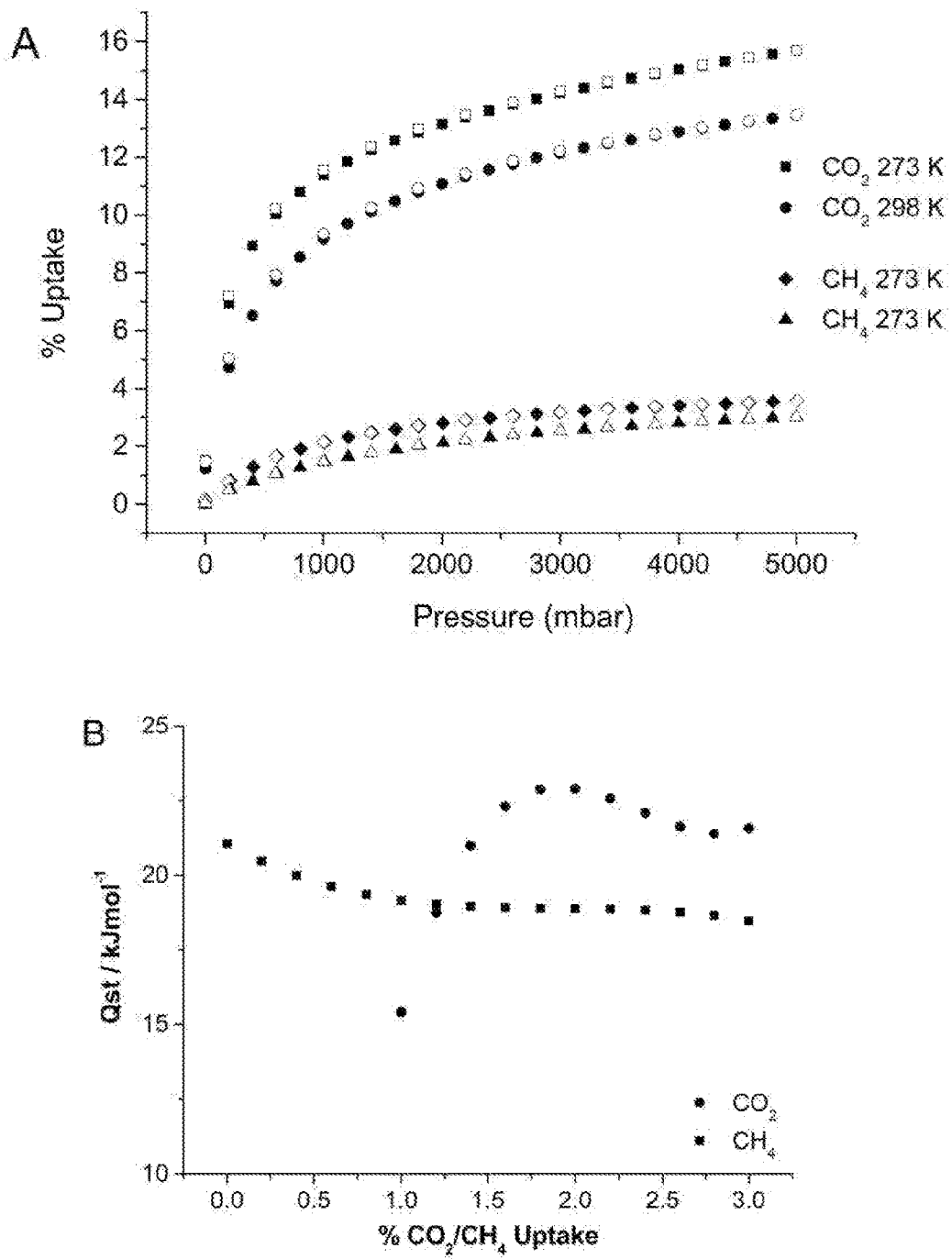
FIG. 8 relates to Isosteric Heat ($Q_{st}$) Determination of compound 2 and shows (a) $CO_2$ and $CH_4$ isotherms collected at 273 K and 298 K; and (b) $CO_2$ and $CH_4 Q_{st}$.

FIG. 8 relates to Isosteric Heat ($Q_{st}$) Determination of compound 2 and shows (a) $CO_2$ and $CH_4$ isotherms collected at 273 K and 298 K; and (b) $CO_2$ and $CH_4 Q_{st}$.

A type I isotherm shows that 2 is permanently porous to $H_2O$ at 295 K and 25 mbar (FIG. 6(b)). The framework is structurally stable following isotherm measurement. It is also stable to immersion in water and subsequent guest removal.

A reversible type 1 isotherm shows that 2 is permanently porous to $CO_2$ at 195 K and 1 bar (FIG. 7(a)). The $CO_2$ isotherm is type I, characteristic of microporous materials[20]. The BET model applied over $p/p_0$=0.02-0.22 gives a surface area of 327 $m^2g^{-1}$ (FIG. 7(b)). The Dubinin-Radushkevich[21] (DR) pore volume of 2 calculated from the $CO_2$ adsorption branch is 0.198 $cm^3g^{-1}$ compared with a pore volume of 0.208 $cm^3g^{-1}$ of the rigid host structure from single crystal data (FIG. 7(c)). A step isotherm shows that 2 is permanently porous to $N_2$ at 77 K and 1 bar (FIG. 6(a)). The isotherm shows a step in adsorption between 50 and 200 mbar which is also apparent in the curve desorption over the same range, however the some hysteresis is seen in the desorption. These factors suggest there may be a phase change with adsorption of $N_2$.

The pore size distribution was calculated by means of an Ar isotherm at standard temperature and pressure, which showed a maximum pore size of 10 Å. This is in good agreement with the pore distances measured from the single crystal structure in which the the smaller of two channels is approximately 8.9×7.9 Å and the larger is 7.0×10.4 Å.

$CO_2$ and $CH_4$ isotherms were also collected for 2 at 273 K and 298 K (FIG. 8(a)). Isosteric heats of adsorption, $Q_{st}$, for $CO_2$ and $CH_4$ were derived from a virial-type expression fitted to the adsorption branches of the isotherms measured at 273 K and 298 K (FIG. 8(b)). The strength of interaction between 2 and the $CO_2$ increases from 18 $kJmol^{-1}$ at zero coverage to 22 $kJmol^{-1}$ at high loading. The interaction between 2 and $CH_4$ decreases from 21.5 $kJmol^{-1}$ at zero coverage to 18 $kJmol^{-1}$ at high loading.

Use of MOFs to Selectively Extract p-Xylene from a Xylene Mixture

Configurational bias Grand Canonical Monte Carlo (GCMC) calculations predicts that 2 should favour pX and EB over mX and oX if structure of 2 is rigid. GCMC simulations have previously been used to understand xylene sorption in zeolites[22,23] and MOFs including MIL-47[24]. More recently these simulations have been used to attempt to predict likely xylene selectivity in MOFs for both sensor[25] and separation applications[26]. Given that the single crystal structure of 2 had been determined, Grand Canonical Monte Carlo (GCMC) simulations were run and pX and mX were subsequently sorbed into the crystal structure of 2 using Materials Studio Adsorption Locator to establish whether they would fit into the channels of the desolvated structure. These predicted that pX would fit into 2, but mX would not, implying that 2 should be selective to pX and could be used to separate from a mixture from both pX and mX isomers.

An initial set of experiments were carried out on all isomers individually (pX, mX, oX and EB) to ascertain whether the framework would take up each isomer. 100 mg of 1 was activated at 100° C. under vacuum overnight after which time 1 mL of pX, mX, oX, or EB was added separately under $N_2$ and left for 24 hours.

Figure 9:
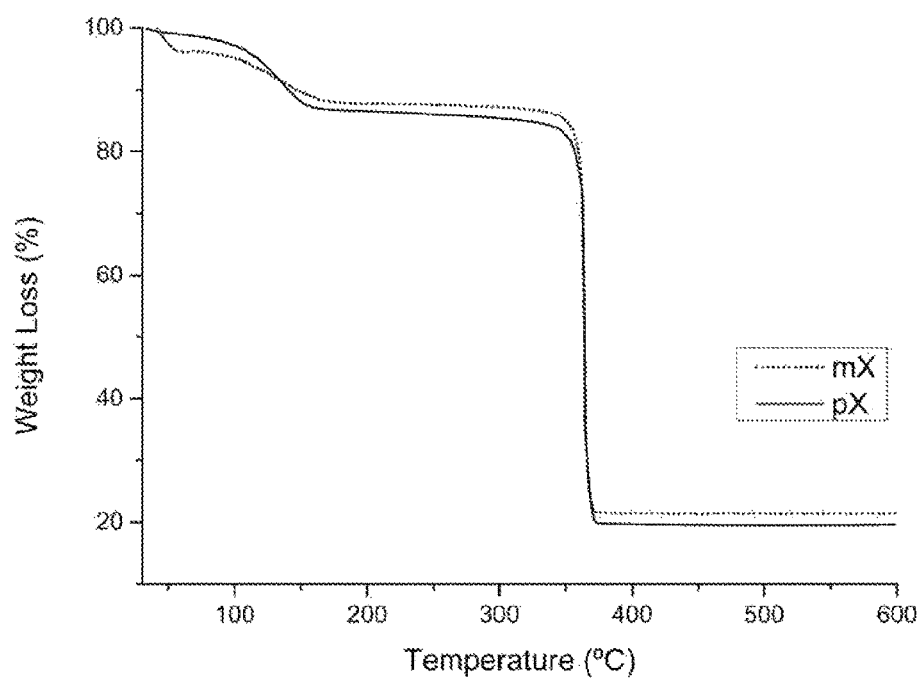
FIG. 9 shows TGA profiles of loaded 2 with pX and mX individually.

FIG. 9 shows TGA profiles of loaded 2 with pX and mX individually.

TABLE 2

CHN and TGA data for xylene loaded 2.

| Experiment | Formula | Theory/% | Found/% | Solvent content from CHN/% | Solvent content from TGA/% |
|---|---|---|---|---|---|
| mX 24 hours | Ce(HTCPB)•0.42(mX)0.37($CH_2Cl_2$)1.47($H_2O$) | C: 56.78<br>H: 3.39 | C: 56.76<br>H: 3.36 | 12.84 | 12.05 |
| pX 24 hours | Ce(HTCPB)•0.65(pX)0.37($CH_2Cl_2$)2.10($H_2O$) | C: 57.58<br>H: 3.73 | C: 57.59<br>H: 3.80 | 13.50 | 13.00 |

TGA and CHN analysis (see FIG. 9 and Table 2) show loadings of 65.5, 42.3, 95.7 and 65.5% for pX, mX, oX and EB respectively (values based on total solvent accessible volume per unit cell from single crystal structure of 2 of 405 $Å^3$ and known volume of a xylene molecule of 204 $Å^3$ in conjunction with amount of xylene present calculated from CHN and TGA), taking into account we expect two xylenes to be taken up per unit cell; one in each channel (one per formula unit). From these experiments, it appears order of preference to enter 2 falls in the order oX>pX=EB>mX.

In order to test the selectivity of 2 towards the 4 $C_8$ isomers, a protocol was set up for screening xylene separation. 100 mg of 1 was activated at 100° C. under vacuum overnight in a Schlenk tube to give 2. 1 mL of equimolar solutions were then added to 2 under $N_2$ and left for 24 hours after which time they were filtered and washed with dichloromethane. All loaded frameworks were characterised for xylene uptake by TGA (FIG. 10(b)) and CHN microanalysis (Table 3).

Figure 10:
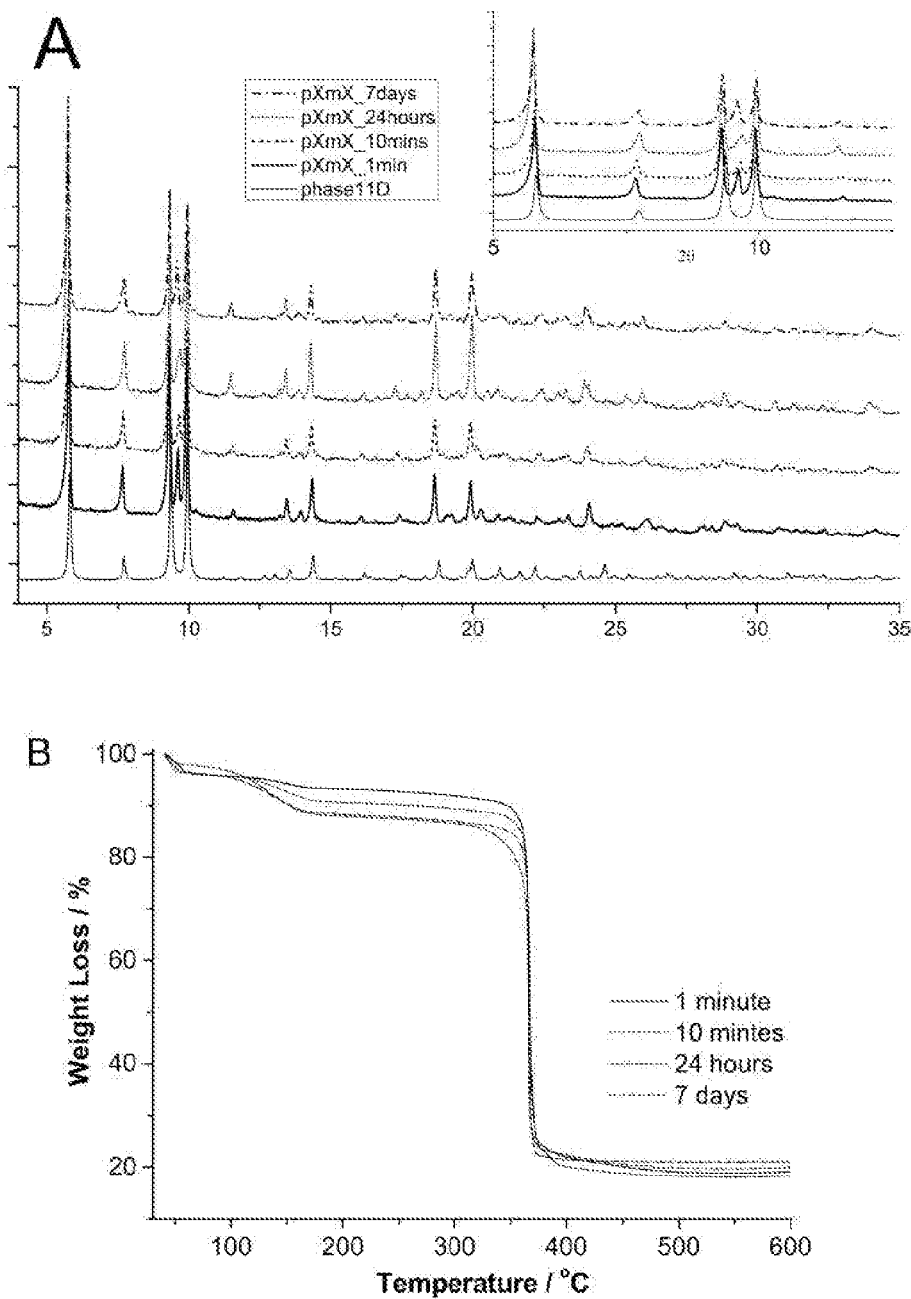
FIG. 10 shows (a) Powder x-ray diffraction profiles of loaded material following xylene uptake experiments on compound 2; and (b) TGA profiles of loaded material following xylene uptake experiments on compound 2.

FIG. 10 shows (a) Powder x-ray diffraction profiles of loaded material following xylene uptake experiments on compound 2; and (b) TGA profiles of loaded material following xylene uptake experiments on compound 2.

TABLE 3

CHN microanalysis for xylene loaded samples of 2.

| Time/Formula | Theory (%) | Found (%) | Solvent content from CHN (%) | Solvent content from TGA (%) |
|---|---|---|---|---|
| 1 minute<br>Ce(HTCPB) $(C_8H_{10})_{0.39}$ $(H_2O)_{0.20}$ $(CH_2Cl_2)_{0.08}$ | C: 56.33<br>H: 3.10 | C: 56.33<br>H: 3.07 | 9.0 | 7.5 |
| 10 minutes<br>Ce(HTCPB) $(C_8H_{10})_{0.46}$ $(H_2O)_{1.25}$ $(CH_2Cl_2)_{0.41}$ | C: 57.06<br>H: 3.38 | C: 57.06<br>H: 3.35 | 10.5 | 10.1 |
| 24 hours<br>Ce(HTCPB) $(C_8H_{10})_{0.65}$ $(H_2O)_{0.68}$ $(CH_2Cl_2)_{0.05}$ | C: 60.36<br>H: 3.43 | C: 60.35<br>H: 3.48 | 13.9 | 13.5 |

TABLE 3-continued

CHN microanalysis for xylene loaded samples of 2.

| Time/Formula | Theory (%) | Found (%) | Solvent content from CHN (%) | Solvent content from TGA (%) |
|---|---|---|---|---|
| 7 days Ce(HTCPB) $(C_8H_{10})_{0.70}$ $(H_2O)_{0.61}$ $(CH_2Cl_2)_{0.07}$ | C: 60.55 H: 3.50 | C: 60.51 H: 3.48 | 13.6 | 13.5 |

The loaded frameworks were then broken down with 1 M NaOH solution and filtered, leaving an aqueous solution of the ligand ($Na_3TCPBH$) and the xylenes. The xylenes were then extracted by washing three times with dichloromethane, dried with $MgSO_4$ and filtered ready for GC analysis. The selectivity ($\alpha_{AB}$) was calculated for each product solution. All resultant xylene solutions were run against a standard equimolar solution of A and B, depending on the mixture under investigation (Table 4).

TABLE 4

Selectivity of 2 towards mixtures of pX, mX, oX and EB.

| | | A | | | |
|---|---|---|---|---|---|
| | | oX | mX | pX | EB |
| B | oX | — | 1.224 | 0.177 | 0.643 |
| | mX | 0.817 | — | 0.223 | 0.420 |
| | pX | 5.652 | 4.481 | — | 2.380 |
| | EB | 1.559 | 2.380 | 0.420 | — |

Selectivities (a) worked out $\alpha_{AB}=(Y_A/Y_B)/(X_A/X_B)$, where $Y_A$ and $Y_B$ are mole fractions of absorbed phase and $X_A$ and $X_B$ are mole fractions of initial phase A and B respectively.

Controls carried out to ensure that no part of the procedure was affecting the selectivity outcome included subjecting an equimolar mixture of pX and mX to the same procedure in the absence of 2. This experiment showed that the xylene mixture after the experiment had the same pX:mX composition as before the experiment, indicating that the protocol does not affect the selectivity observed. This means the selectivity observed in the xylene separation experiments is entirely due to the presence of the MOF. In order to ensure DCM had no effect on the framework, a separate experiment was carried out in which 2 was exposed to DCM, left for 24 hours and then filtered, which showed the framework remained unchanged, characterised by PXRD.

These batch measurements show selectivity in the order pXoX>pXmX>EBmX=pXEB>oXmX>mXoX>mXEB=EB pX>mXpX>oXpX with a record $\alpha_{pXmX}$ of 4.481, $\alpha_{pXoX}$ of 5.65 and $\alpha_{pXEB}$ of 2.4. These values can be compared to the best performing zeolite in xylene separation, KBaY, which shows $\alpha_{pXmX}$ and $\alpha_{pXEB}$ of 3.75 and 2.1 respectively. These values can be compared to the best performing MOF and zeolite in xylene separation (see Table 7 below).

Further analytical data obtained in relation to these sorption complexes is detailed below:

Ce(HTCPB)·$(pXEB)_{0.75}(DCM)_{0.22}(H_2O)_{0.16}$ Calc C: 60.63 H: 3.45 Observed C: 60.62 H: 3.32 TGA mass loss expected 12.70% found 12.75%.

Ce(HTCPB)·$(pXmX)_{0.74}(DCM)_{0.16}(H_2O)_{0.11}$ Calc C: 60.95 H: 3.45 Observed C: 60.95 H: 3.36 TGA mass loss expected 11.92% found 12.25%.

Ce(HTCPB)·$(pXoX)_{0.75}(DCM)_{0.13}(H_2O)_{0.10}$ Calc C: 61.16 H: 3.45 Observed C: 61.13 H: 3.39 TGA mass loss expected 11.73% found 12.04%.

Ce(HTCPB)·$(mXEB)_{0.55}(DCM)_{0.15}(H_2O)_{0.23}$ Calc C: 60.06 H: 3.30 Observed C: 60.06 H: 3.31 TGA mass loss expected 9.76% found 9.18%.

Ce(HTCPB)·$(mXoX)_{0.55}(DCM)_{0.11}(H_2O)_{0.62}$ Calc C: 59.72 H: 3.38 Observed C: 59.71 H: 3.36 TGA mass loss expected 10.19% found 9.85%.

Ce(HTCPB)·$(oXEB)_{0.38}(DCM)_{0.33}(H_2O)_{0.44}$ Calc C: 58.15 H: 3.18 Observed C: 58.14 H: 3.15 TGA mass loss expected 9.88% found 9.16%.

With the main aim of research in this area being on the separation of pX and mX, we further investigated the time dependence on the selectivity of 2 towards these two isomers. The times chosen for this series of experiments were 1 minute, 10 minutes and 7 days (Table 2). The procedure used was the same as for the previous batch experiments, and the value for 24 hours was used from the previous experiment.

TABLE 5

Selectivity of 2 towards an equimolar mixture of pX and mX after period of time [a].

| Time [a] | Selectivity, $\alpha_{pXmX}$ [b] | Loading, % [c] |
|---|---|---|
| 1 minute | 3.280 | 8.4 |
| 10 minutes | 3.723 | 29.3 |
| 24 hours | 4.481 | 68.1 |
| 7 days | 4.912 | 73.3 |

[b] Selectivities calculated using equation: $\alpha_{pm} = (Y_p/Y_m)/(X_p/X_m)$, where $Y_p$ and $Y_m$ are mole fractions of absorbed phase and $X_p$ and $X_m$ are mole fractions of initial phase.
[c] Loading calculated by multiplying the number of xylene molecules present per formula unit (calculated from CHN and TGA) by the total accessible volume determined from the single crystal structure of 2.

The results show that 2 is immediately highly selective to pX, with $\alpha_{pXmX}$ of 3.280 after only one minute. This value increases with longer times up to an even higher record $\alpha_{pXmX}$ of 4.912 after 7 days (Table 5). TGA (FIG. 10(b)) and CHN microanalysis (Table 3) show that the extent of loading increases over time, with a loading of 8.4% (0.39) after 1 minute up to 73.3% (0.7) after 7 days, alongside an increase in selectivity.

PXRD analysis (FIG. 10(a)) of the loaded material over these time periods show a shift in structure compared to the original desolvated phase.

Figure 11:
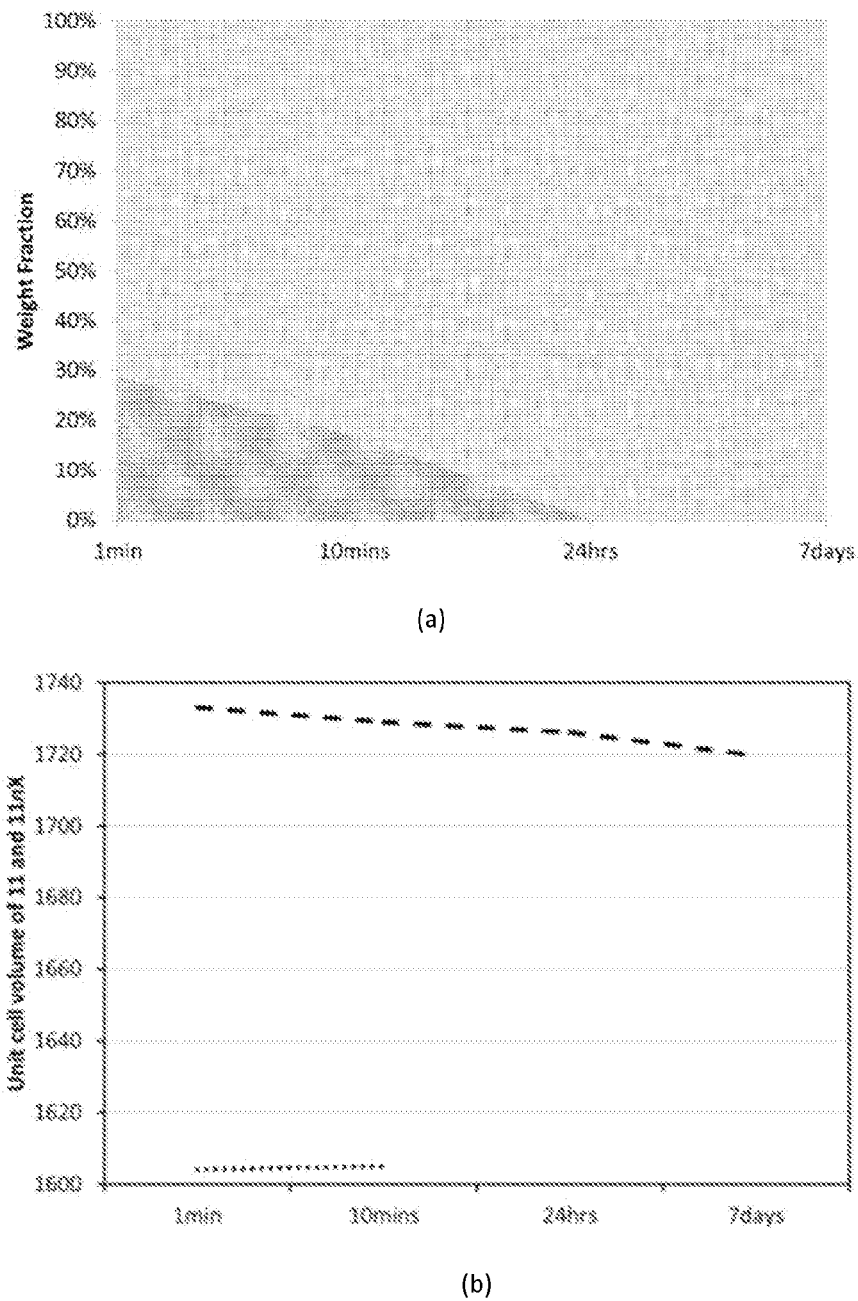
FIG. 11 shows analysis of the relative amounts of compound 2 (red) and xylene loaded compound 2PM (blue) over the time course of the pXmX selectivity experiments.

FIG. 11 shows analysis of the relative amounts of compound 2 (red) and xylene loaded compound 2PM (blue) over the time course of the pXmX selectivity experiments.

Phase 2 is still present at around 30% after 1 minute alongside a 'loaded' phase, 2PM, which has a larger unit cell volume than 2. After 10 minutes, the amount of 2 has reduced to 20% and has completely disappeared by 24 hours. The unit cell volume of 2 increases slightly between 1 and 10 minutes due to loading of the material before conversion to 2PM. Phase 2PM is present at all times throughout the experiment, however the unit cell volume is decreasing with time. This may be due to ordering of the xylene molecules within the channels; initially at 1 minute there is a large amount of disorder so the structure has a larger unit cell volume, but as the xylenes become more ordered and form interactions with the channel walls, the unit cell volume decreases (FIG. 11).

Figure 12:
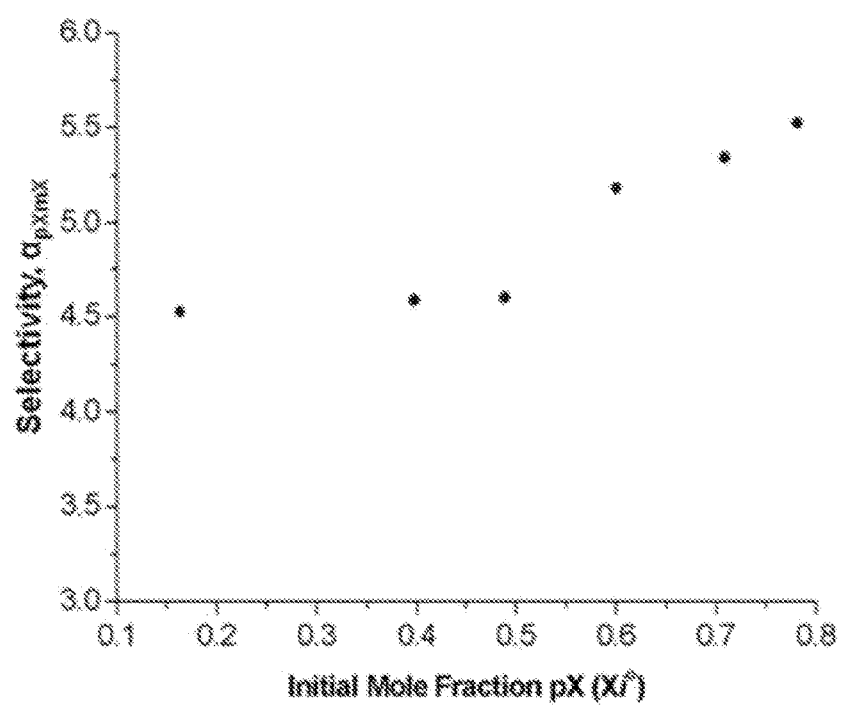
FIG. 12 shows selectivity $\alpha_{pXmX}$ of 2 with increasing pX uptake.

In additional experiments, the pX/mX selectivity of 2 was determined using initial solutions with varying pX/mX ratios (from 0.196 to 3.581) in order to investigate the selectivity of 2. These experiments were carried out for 24 hours using 50 mg of 2 using the same protocol described in section 5.3.2. The pX/mX ratio in the supernatant does not change during these experiments, confirmed by direct GC analysis. The selectivity, $\alpha_{pXmX}$, dependence on pX/mX ratio is shown in FIG. 12. FIG. 12 shows selectivity $\alpha_{pXmX}$ of 2 with increasing pX uptake.

There is enhanced pX/mX selectivity for pX as more pX is loaded into 2. This agrees with the GCMC calculations which predict that 2P is more selective than 2M, so as more pX is introduced to the framework, it becomes more selective to pX.

A series of single crystal diffraction experiments were carried out to determine the structure of the xylene loaded materials for comparison with the GCMC calculations. For xylene loaded 2, single crystals were activated at 100° C. under vacuum overnight after which time pX and mX were added to separate samples respectively. Data were then collected after 24 hours on each sample at 100 K. The data showed the formation of two new phases—2P in the pX loaded material and 2M in the mX loaded material. Table 6 shows the unit cell dimensions of 2, 2P and 2M.

may account for the lower observed pX loading into a single crystal of 2P compared to the whole bulk sample.

PXRD analysis of the loaded material over these time periods show a change in structure compared to the original desolvated phase. Phase 2 is still present at around 30% after 1 minute alongside a 'loaded' phase, 2PM, which has a larger unit cell volume than 2. After 10 minutes, the amount of 2 has reduced to 20% and has completely disappeared by 24 hours. The unit cell volume of 2 increases slightly between 1 and 10 minutes due to loading of the material before conversion to 2PM. Phase 2PM is present at all times throughout the experiment, however the unit cell volume is decreasing with time.

The single crystal structure of 2M again has the same structure as 2, but it has an even larger unit cell volume than both 2 and 2P of 1729.02 Å$^3$. Analysis of the void space in 2M with xylenes removed give a total accessible volume of 501.8 Å$^3$, corresponding to 29.0% of the unit cell volume (compared to 405 Å$^3$ and 24.9% respectively in 2 and 448.9 and 24.9% respectively in 2P). Analysis of the blue and green channels individually show increases in the size of both from 2 and 2P, with the blue channel now being 218.2

TABLE 6

Unit cell dimensions of 2 with xylenes included
Unit Cell Dimensions

| | a/Å | b/Å | c/Å | α/° | β/° | γ/° | V/Å$^3$ |
|---|---|---|---|---|---|---|---|
| 2 | 9.989(11) | 11.4163(13) | 15.2492(17) | 93.756(5) | 90.263(6) | 93.814(6) | 1611.7(3) |
| 2P | 9.5603(4) | 12.1386(5) | 15.9458(10) | 88.455(10) | 74.417(10) | 70.233(10) | 1673.27(12) |
| 2M | 9.7441(6) | 12.3318(7) | 15.7737(9) | 88.979(2) | 77.299(2) | 69.498(2) | 1729.02(18) |

Structure analysis of 2P shows that the core structure is the same as 2 but with a larger unit cell volume due to the inclusion of pX into the framework; 2 has a unit cell volume of 1632.08 Å$^3$, which increases to 1673.27 Å$^3$ in 2P. Analysis of the void space in 2P with xylenes removed give a total accessible volume of 448.9 Å$^3$, corresponding to 26.8% of the unit cell volume (compared to 405 Å$^3$ and 24.9% respectively in 2). Analysis of the blue and green channels individually show increases in the size of both from 2, with the blue channel now being 206.4 and the green being 242.5 Å$^3$ compared to 186.2 Å$^3$ and 218.8 Å$^3$ respectively in 2. This shows an overall expansion in the void space from 2 to 2P, consequential of pX inclusion into the framework. Within the structure of 2P, two crystallographically unique pX molecules are present within the two independent channels referred to as green and blue (as discussed for 2), which both refine to 100% occupancy. Both xylenes line up down the channels along the a-axis, and within the blue channel, the central aromatic ring of pX forms a π . . . H—C interaction with an H-atom of a HTCPB ligand. In the green channel, such interactions are less pronounced due to the channel being larger, however deviation of the structure from 2 allows for pX molecules in both channels to fit in exactly. This agrees with the calculations which predict that pX can enter 100% of the channel space of 2, and the orientation of the pX molecules within the channels also agrees with the lowest energy docking site in the GCMC calculations. However TGA and CHN analysis of 2P after soaking a sample of 2 in pX for 24 hours show a loading of 68.1%. The loading of the framework over the course of the experiments implies that the kinetics of xylene diffusion into the framework are relatively slow, with only a slight increase to 73.3% loading after 7 days from that at 24 hours, and this Å$^3$ and the green being 283.6 Å$^3$ compared to 186.2 Å$^3$ and 218.8 Å$^3$ respectively in 2 and 206.4 Å$^3$ and 242.5 Å$^3$ respectively in 2P). The framework has had to distort to a greater extent in the case of 2M due to the inclusion of the larger mX and its disordered presence within both channels. In the blue channel, the molecule is disordered about the central aromatic ring, and occupies a total volume of 125 Å$^3$ at isolated 'pinch points' along the 1D channel. In the green channel, mX is disordered over two positions across an inversion centre occupying 135 Å$^3$, and the whole disordered molecule is disordered throughout the length of the channel. However, the relative occupancies of both mX molecules are 100% and 50% in the blue and green channels respectively giving an average amount of 75% mX per formula unit (compared to 100% occupancy of pX in 2P).

Bulk analysis of 2M shows a loading of 42.3%, which is lower than that observed in the single crystal structure, as was seen in the case of 2P. This again may be due to diffusion within the bulk sample, limiting how much becomes fully loaded with xylene. A larger distortion from 2 must occur to reach 2M than 2P, so within the bulk sample, this would happen at a slower rate for 2M than for 2P, hence why a lower loading is seen for mX in 2M after 24 hours than pX in 2P.

The GCMC calculations predicted that no mX would fit into 2, however the large expansion in unit cell volume between 2 and 2M accounts for this uptake. Calculations re-run on 2M with all xylene molecules removed show an uptake of mX into the larger green channel but no uptake into the smaller blue channel meaning theoretically based on this structure we could expect a maximum loading of 50% mX.

The calculated uptakes are less than observed if 2 is rigid. However measurement the structure of 2 exposed to mX and pX an show increase in cell volumes from 2 and distortion, larger in the case of mX case due to its larger kinetic diameter. Different expansion is seen in the green and blue channels; the channel space becomes distinct depending on the structure of the guests, permitting uptake of more guest than for the rigid host but retaining the separating power to a level higher than in any other material. In 2 both the green and blue channels can take up pX but neither can uptake mX. But in 2P and 2M both channels are accessed by expansion while retaining high selectivity: the channels are large enough to admit xylene after expansion but specific enough to separate them.

Selectivity of Cerium MOF Compared to MOFs of the Prior Art

Table 7 shows the xylene selectivity performance of cerium MOFs of the invention as compared to MOFs of the prior art.

TABLE 7

Comparison of xylene-separation selectivities for various MOFs

| MOF | pX uptake (wt %) | mX uptake (wt %) | Selectivity[27] ($\alpha_{pm}$) | Volume absorbed $V_\alpha$ (cm$^3$g$^{-1}$) | Selectivity ($\alpha_{ij}$) $\alpha_{pXmX}$ | $\alpha_{pXoX}$ | $\alpha_{pXEB}$ |
|---|---|---|---|---|---|---|---|
| Ce(HTCPB) | 11.32 | 8.67 | 4.912 | 0.09 | | | |
| NaY | | | | 0.284[28] | | | |
| KY | | | | 0.271[28] | 4.5 | | |
| KBaY | 15 | 3.2 | 4.0 | 0.238[28] | 4.0 | | 2.1 |
| MIL-125(Ti)-NH$_2$ | 12[a] | 4[a] | 4.41[a] | | 3.5 | 2.2 | |
| CAU-1(Al)-NH$_2$ | | | 2.81[a] | | | | |
| MIL-125(Ti) | | | 3.51[a] | | | | |
| MIL-47 (high p) | | | 2.073[b] | | 2.9 | 0.7 | 9.7 |
| MIL-49 | | | 2.92[c] | | | | |
| MIL-53(Al)ht (high p) | 37[29] | 36[29] | 0.82[c] | | 0.8 | 0.3 | 3.1 |
| HKUST-1 | | | 0.92[c] | | 0.9 | 1.4 | 1.2 |

[a]Liquid: 0.028M solution xylene in heptanes;
[b]Vapour phase;
[c]Liquid phase separation achieved in hexane.

Other materials which have been shown to separate pX from a mixture of pX and mX in the vapour or liquid phase with selectivities quoted in the same way as discussed for Ce(HTCPB) using the formula are $\alpha_{AB}=(Y_A/Y_B)/(X_A/X_A)$, where $Y_A$ and $Y_A$ are mole fractions of absorbed phase and $X_A$ and $X_B$ are mole fractions of initial phase A (pX) and B (mX) respectively are:

Zeolite KBaY with $\alpha_{AB}$=4,[27] MIL-125(Ti)—NH$_2$ with $\alpha_{AB}$=4.4, CAU-1(Al)—NH$_2$ with $\alpha_{AB}$=2.8, MIL-125(Ti) with $\alpha_{AB}$=3.5, MIL-47 (high pressure) with a$_{AB}$=2.07, MIL-49 with $\alpha_{AB}$=2.9, MIL-53ht (high pressure) with $\alpha_{AB}$=0.82 and HKUST-1 with $\alpha_{AB}$=0.92.

Example 2—Further Lanthanide MOFs

Preparation of Lanthanide MOFs

Various lanthanide MOFs conforming to the general formula Ln(HTCPB), where Ln represents a lanthanide 3+ ion, were synthesised using the same experimental procedure as for Ce(HTCPB) in Example 1. As such, 20 mg Ln(III) (NO$_3$)$_3$.6H$_2$O, 10 mg H$_4$TCPB in EtOH (3 mL) and H$_2$O (3 mL) were mixed and heated to 120° C. for 48 hours, yielding single crystals of MOF.

Performance of Lanthanide MOFs in p-Xylene Extractions

The relative xylene selectivities for the different lanthanide MOFs were then tested in the same manner as per Example 1, yielding the results shown in Table 8.

TABLE 8

Xylene selectivities for a range of lanthanides

| CHN Theory: | Found: | Formula | Selectivity ($\alpha$pXmX) |
|---|---|---|---|
| C 59.64 | C 59.64 | La(HTCPB)(C$_8$H$_{10}$)$_{0.80}$(CH$_2$Cl$_2$)$_{0.50}$(H$_2$O)$_{0.10}$ | 5.085 |
| H 3.45 | H 3.48 | | |
| C 59.54 | C 59.54 | Ce(HTCPB)(C$_8$H$_{10}$)$_{0.81}$(CH$_2$Cl$_2$)$_{0.49}$(H$_2$O)$_{0.18}$ | 6.010 |
| H 3.47 | H 3.37 | | |
| C 58.79 | C 58.79 | Pr(HTCPB)(C$_8$H$_{10}$)$_{0.83}$(CH$_2$Cl$_2$)$_{0.70}$(H$_2$O)$_{0.03}$ | 6.359 |
| H 3.43 | H 3.34 | | |
| C 59.83 | C 59.83 | Nd(HTCPB)(C$_8$H$_{10}$)$_{0.87}$(CH$_2$Cl)$_{0.44}$(H$_2$O)$_{0.09}$ | 6.202 |
| H 3.49 | H 3.46 | | |

TABLE 8-continued

Xylene selectivities for a range of lanthanides

| CHN Theory: | Found: | Formula | Selectivity ($\alpha$pXmX) |
|---|---|---|---|
| C 56.77 | C 56.77 | Sm (HTCPB)(C$_8$H$_{10}$)$_{0.88}$(CH$_2$Cl$_2$)$_{1.08}$(H$_2$O)$_{0.01}$ | 6.109 |
| H 3.39 | H 3.16 | | |
| C 56.24 | C 56.24 | Eu (HTCPB)(C$_8$H$_{10}$)$_{0.90}$(CH$_2$Cl$_2$)$_{0.55}$(H$_2$O)$_{2.33}$ | 3.460 |
| C 3.82 | H 3.86 | | |

Selectivities are calculated as for Ce(HTCPB) using formula $\alpha_{AB}=(Y_A/Y_B)/(X_A/X_B)$, where $Y_A$ and $Y_A$ are mole fractions of absorbed phase and $X_A$ and $X_B$ are mole fractions of initial phase A (pX) and B (mX) respectively.

The cerium species of Table 8 is similar to that described in Example 1, only with different crystallite sizes. The Ce(HTCPB) of Example 1 was produced as a pure phase but in microcrystalline form, with particle sizes ranging from 2-20 µm, via the 3× scaled—up process described in Example 1. The Ce(HTCPB) used in table 8 was synthesised using the non-scaled-up process of Example 1, in which large single crystals with a particle size around 50 µm were produced.

The selectivity results presented herein demonstrate the superior selectivity of Cerium-MOFs as compared to the prior art, and also demonstrate that other lanthanide-MOFs perform substantially as well as the Cerium-MOFs.

A further pX/mX sorption selectivity study of isostructural Ln(HTCPB) MOFs was conducted, where Ln=La, Pr, Nd and Sm. The selectivities of the Ln(HTCPB) MOFs (isostructural to compound 2) were determined using the same batch liquid sorption procedure as described above in relation to the selectivity tests upon compound 2. After 24 hours, the selectivity was highest for Ln=Nd (see Table 9 below), contrary to rigid lattice GCMC calculations which predict that 3-Ce should be more selective.

TABLE 9

$\alpha_{pXmX}$ selectivities of a series of isostructural Ln(HTCPB) compounds denoted 3-Ln.

| Ln | Selectivity $\alpha_{pXmX}$ |
| --- | --- |
| 3-La | 4.48 (7) |
| 3-Ce (2) | 4.55 (6) |
| 3-Pr | 6.15 (3) |
| 3-Nd | 6.33 (3) |
| 3-Sm | 6.08 (4) |

REFERENCES

1. Vermoortele, F, Maes, M, Moghadam, P, Lennox, M, Ragon, F, Boulhout, M, Biswas, S, Laurier, K, Beurroies, I, Denoyel, R, Roeffaers, M, Stock, N, Duren, T, Serre, C, & De Vos, D n.d., 'p-Xylene-Selective Metal-Organic Frameworks: A Case of Topology Directed Selectivity', Journal Of The American Chemical Society, 133, 46, pp. 18526-18529, Science Citation Index, EBSCO host, viewed 5 Mar. 2012.
2. Alaerts, L, Kirschhock, C, Maes, M, van der Veen, M, Finsy, V, Depla, A, Martens, J, Baron, G, Jacobs, P, Denayer, J, & De Vos, D 2007, Selective adsorption and separation of xylene isomers and ethylbenzene with the microporous vanadium(IV) terephthalate MIL-47, Angewandte Chemie-International Edition, 46, 23, pp. 4293-4297, Science Citation Index, EBSCOhost, viewed 5 Mar. 2012.
3. Finsy et al., 'Pore-filling-dependent selectivity effects in the vapor-phase separation of xylene isomers on the metal-organic framework MIL-47', Journal Of The American Chemical Society, 130, 22, pp. 7110-7118, Science Citation Index, EBSCOhost, viewed 5 Mar. 2012.
4. US EPA1994. [ONLINE] Available at: http://www.epa.gov/ttnchiel/le/xylene.pdf. [Accessed 10 Jan. 2012].
5. Lima R, Grossmann I. Optimal Synthesis of p-Xylene Separation Processes Based on Crystallization Technology. Aiche Journal [serial online]. February 2009; 55(2): 354-373. Available from: Computers & Applied Sciences Complete, Ipswich, Mass. Accessed Jan. 3, 2012.
6. Cannella W. Kirk-Othmer Encyclopedia of Chemical Technology, chapter Xylenes and ethylbenzene. John Wiley & Sons. 2001.
7. Lima R, Grossmann I. Optimal Synthesis of p-Xylene Separation Processes Based on Crystallization Technology. Aiche Journal [serial online]. February 2009; 55(2): 354-373. Available from: Computers & Applied Sciences Complete, Ipswich, Mass. Accessed Jan. 3, 2012.
8. Wantanachaisaeng et al, 2007, Capturing Opportunities for Para-xylene Production [ONLINE] Available at: http://www.uop.com/wp-content/uploads/2010/12/UOP-aromatics-paraxylene-capture-paper1.pdf. [Accessed 3 Jan. 2012].
9. US Patent Publication No. 20110420779 (UOP LLC)
10. Yang, C, & Yan, X n.d., 'Metal-Organic Framework MIL-101(Cr) for High-Performance Liquid Chromatographic Separation of Substituted Aromatics', Analytical Chemistry, 83, 18, pp. 7144-7150, Science Citation Index, EBSCOhost, viewed 5 Mar. 2012.
11. Moreira et al, "Reverse Shape Selectivity in the Liquid-Phase Adsoprtion of Xylene Isomers in Zirconium Terephthalate MOF UiO-66", Langmuir, 2012, 28, 5715-5723.
12. Chin, C. Y. & Wang N-H. L., Separation and Purification Reviews, Vol. 33, No. 2, p. 77-155, 2004.
13. Alaerts, deVos, Angewandte Chemie International Edition, Volume 46, Issue 23, pages 4293-4297, Jun. 4, 2007.
14. CrystalClear-SM Expert 2.0 r5—Rigaku, 2010.
15. FS Process—T Higashi, 2001.
16. SADABS 2008/4—Bruker, 2010.
17. Olex2—O. V. Dolomanov, L. J. Bourhis, R. J. Gildea, J. A. K. Howard and H. Puschmann, J. Appl. Cryst., 2009, 42, 339-341.
18. Shelxl—G. M., Sheldrick Acta Cryst., 2008, A64, 112-122.
19. Farha, O. K.; Malliakas, C. D.; Kanatzidis, M. G.; Hupp, J. T.; J. Am. Chem. Soc., 2010, 132, 950.
20. Rouquerol, F.; Rouquerol, J.; Sing, K., Adsorption by Powders and Porous Solids, Academic Press, London, 1999.
21. Tovbin, Y. K., Russ. Chem. Bull., 1998, 47, 637.
22. Lachet, V.; Boutin, A.; Tavitian, B.; Fuchs, A. H., Langmuir, 1999, 15, 8678.
23. Chempath S.; Snurr, R. Q.; Low, J. J., AIChE, 2004, 50, 463.
24. Castillo, J. M.; Vlugt, T. J. H.; Calero, S., J. Phys. Chem. C, 2009, 113, 20869.
25. Greathouse, J. A.; Ockwig, N. W.; Criscenti, L. J.; Guilinger, T. R.; Pohl, P.; Allendorf, M. D., PCCP, 2010, 12, 12621.
26. Krishna, R.; van Baten, J. M., PCCP, 2011, 13, 10593.
27. A. Methivier in Zeolites for Cleaner Technologies, Catalytic Science Series—Vol. 3 (Eds.: M. Guisnet, J. P. Gilson), Imperial College Press, London, 2002, pp. 209-221.
28. Bellat, Zeolites 15: 1995, 219-227, 224.
29. "Metal Organic Frameworks", David Farrusseng, Wiley-VCH, First Edition, 2011, p. 185.

What is claimed is:
1. A method of separating a desired component from a mixture of components, the method comprising:
    selectively sorbing a desired component from a mixture of components by contacting the mixture of components with a sorbent material to selectively sorb the desired component within/to the sorbent material to produce a sorption complex;
    removing any non-sorbed component(s) from contact with the sorption complex; and
    optionally recovering the desired component from the sorption complex;
wherein the mixture of components comprises p-xylene and m-xylene; and
wherein the sorbent material comprises a metal-organic framework (MOF), which metal-organic framework comprises a compound comprising:

an f-block metal ion (M); and a polydentate ligand (LIG) able to co-ordinate with M to provide a metal organic framework (MOF) structure;

wherein the LIG group is defined by Formula A (or a suitable ionised form thereof):

CORE-[-L-R]$_n$ (Formula A)

wherein:

n is an integer between 1 and 6 such that n individual and independently defined -L_R groups (i.e. $L_1$-$R_1$ . . . $L_n$-$R_n$) are attached to CORE;

CORE comprises one or more aromatic or heteroaromatic systems;

each L group is the same or different, each being independently either absent or a linker selected from the group including (1-3C)alkylene, (2-3C)alkenylene, (2-3C)alkynylene, O, S, SO, $SO_2$, N($R'_a$), CO, CH($OR'_a$), CON($R'_a$), N($R'_a$)CO, N($R'_a$)CON($R'_a$), $SO_2$N($R'_a$), N($R'_a$)$SO_2$, OC($R'_a$)$_2$, SC($R'_a$)$_2$ and N($R'_a$)C($R'_b$)$_2$, wherein $R'_a$ and $R'_b$ are each independently hydrogen or (1-8C)alkyl;

each R group is the same or different, each being independently selected from an aryl or heteroaryl group bearing a lone pair of electrons capable of coordinating with M or substituted by a group bearing a lone pair of electrons capable of coordinating with M;

wherein CORE or any R group is optionally further substituted by one or groups selected from halogeno, trifluoromethyl, trifluoromethoxy, cyano, isocyano, nitro, hydroxy, mercapto, amino, formyl, carboxy (incl. carboxylic acid), carbamoyl, ureido, sulphonyl (incl. sulphonic acid), phosphoryl (incl. phosphonic acid), (1-8C)alkyl, (2-8C)alkenyl, (2-8C)alkynyl, (1-8C)alkoxy, (2-8C)alkenyloxy, (2-8C)alkynyloxy, (1-8C)alkylthio, (1-8C)alkylsulphinyl, (1-8C)alkylsulphonyl, (1-8C)alkylamino, di-[(1-8C)alkyl]amino, (1-8C)alkoxycarbonyl, N-(1-8C)alkylcarbamoyl, N,N-di-[(1-8C)alkyl]carbamoyl, (2-8C)alkanoyl, (2-8C)alkanoyloxy, (2-8C)alkanoylamino, N-(1-8C)alkyl-(2-8C)alkanoylamino, (3-6C)alkenoylamino, N-(1-6C)alkyl-(3-6C)alkenoylamino, (3-6C)alkynoylamino, N-(1-6C)alkyl-(3-6C)alkynoylamino, N'-(1-6C)alkylureido, N',N'-di-[(1-6C)alkyl]ureido, N-(1-6C)alkylureido, N,N'-di-[(1-6C)alkyl]ureido, N,N',N'-tri-[(1-6C)alkyl]ureido, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino;

or an (acceptable) salt and/or solvate thereof.

2. The method as claimed in claim 1, wherein p-xylene is the desired component.

3. The method as claimed in claim 1, wherein the f-block metal ion (M) is a lanthanide metal ion.

4. The method as claimed in claim 3, wherein the f-block metal ion is selected from a lanthanum, cerium, praseodymium, neodymium, samarium, or europium ion.

5. The method as claimed in claim 1, wherein the f-block metal ion is cerium (III)—i.e. $Ce^{3+}$.

6. The method as claimed in claim 1, wherein CORE is a benzene ring, optionally substituted as defined in claim 1.

7. The method as claimed in claim 6, wherein the LIG group is defined by Formula B (or a suitable ionised form thereof), optionally further substituted as defined in claim 1:

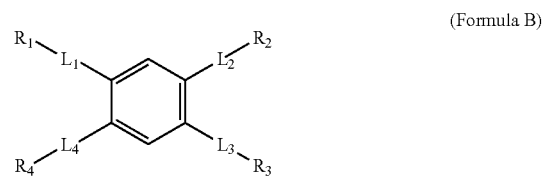

where the L and R groups (i.e. $L_1$, $L_2$, $L_3$, $L_4$, and $R_1$, $R_2$, $R_3$, $R_4$) are as defined in claim 1.

8. The method as claimed in claim 1, wherein the LIG group is selected from any one of (or a suitable ionised form of):

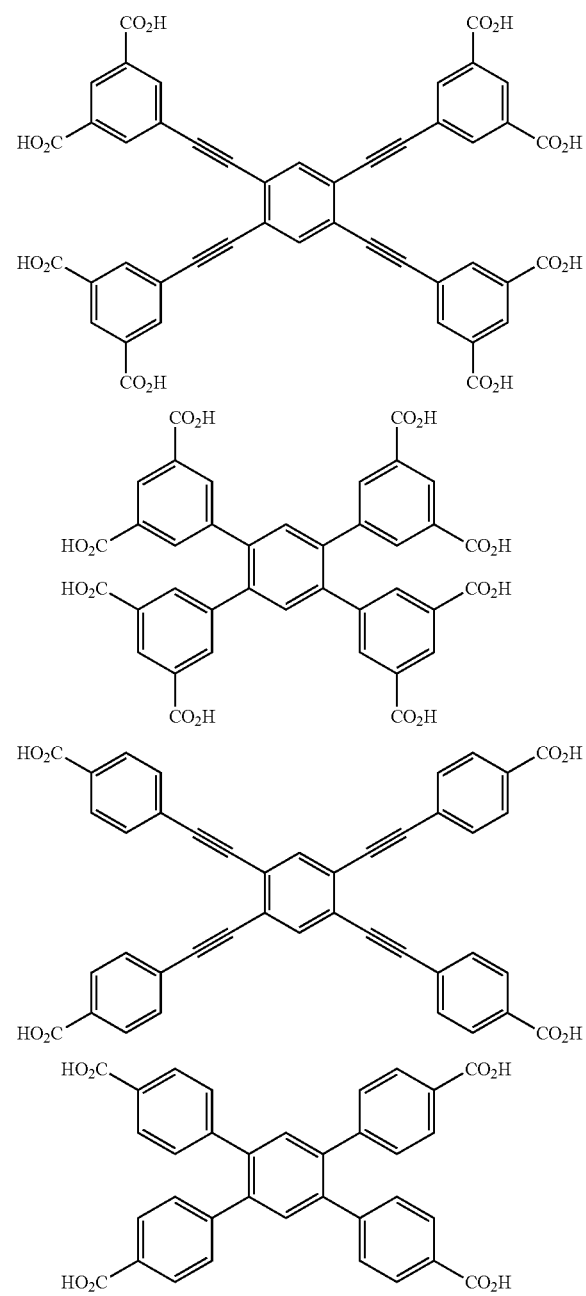

-continued
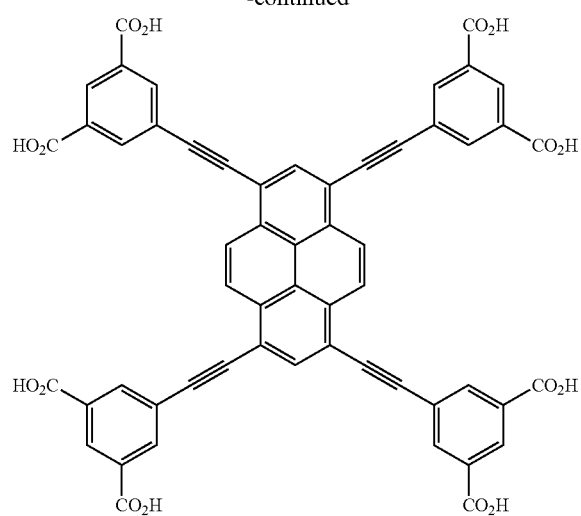
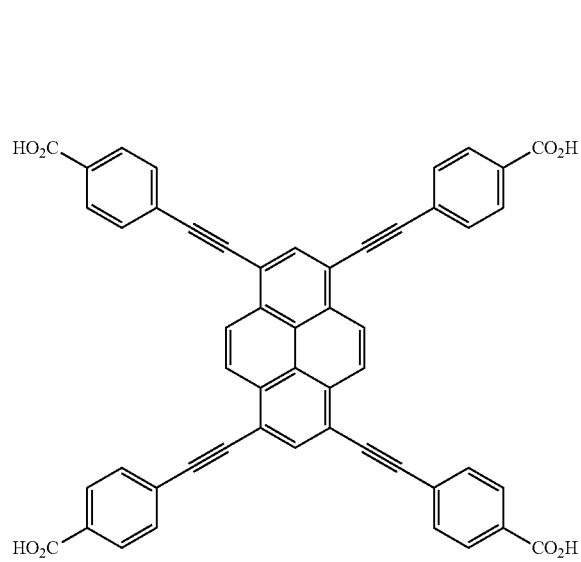
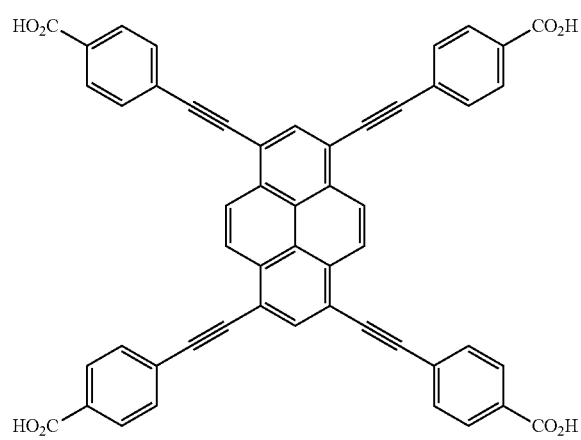
-continued
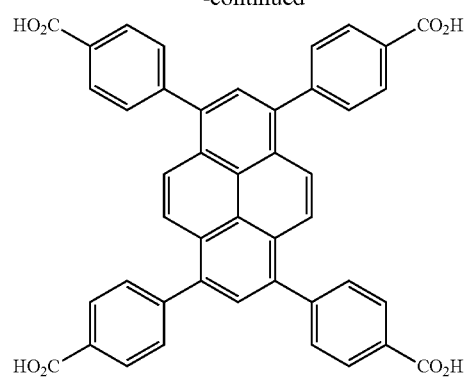
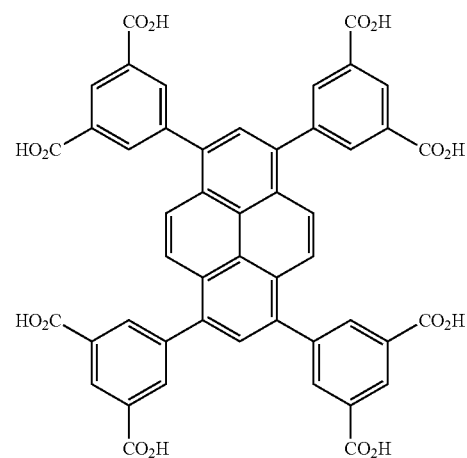

-continued

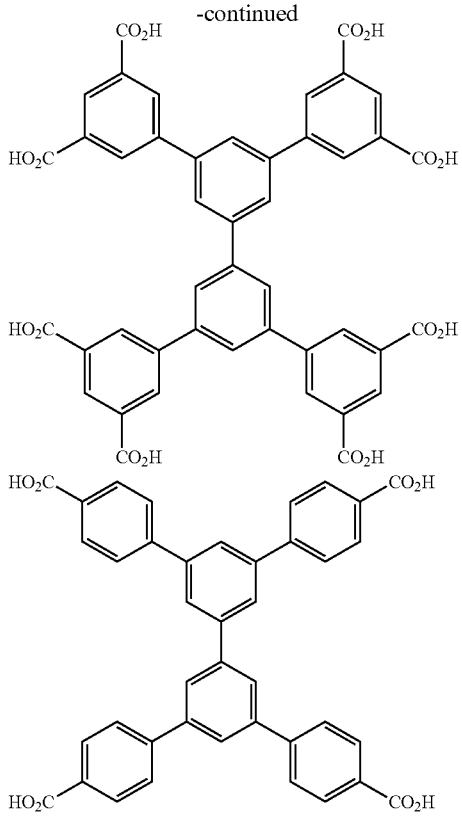

optionally further substituted as defined in claim 1.

9. The method as claimed in claim 1, wherein the LIG group is (or a suitable ionised form of):

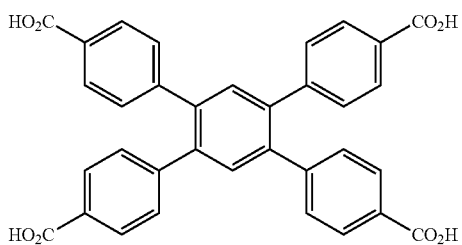 [SMILES: O=C(O)c1ccc(-c2cc(-c3ccc(C(=O)O)cc3)c(-c3ccc(C(=O)O)cc3)cc2-c2ccc(C(=O)O)cc2)cc1]

optionally further substituted as defined in claim 1.

10. A method of selectively sorbing a desired component from a mixture of components, the method comprising contacting the mixture of components with a sorbent material comprising a metal-organic framework (MOF), which metal-organic framework comprises a compound comprising:

an f-block metal ion (M); and
a polydentate ligand (LIG) able to co-ordinate with M to provide a metal organic framework (MOF) structure; wherein the LIG group is defined by Formula A (or a suitable ionised form thereof):

$$CORE\text{-}[\text{-}L\text{-}R]_n \quad \text{(Formula A)}$$

wherein:
n is an integer between 1 and 6 such that n individual and independently defined -L_R groups (i.e. $L_1\text{-}R_1 \ldots L_n\text{-}R_n$) are attached to CORE;
CORE comprises one or more aromatic or heteroaromatic systems;
each L group is the same or different, each being independently either absent or a linker selected from the group including (1-3C)alkylene, (2-3C)alkenylene, (2-3C)alkynylene, O, S, SO, $SO_2$, $N(R'_a)$, CO, $CH(OR'_a)$, $CON(R'_a)$, $N(R'_a)CO$, $N(R'_a)CON(R'_a)$, $SO_2N(R'_a)$, $N(R'_a)SO_2$, $OC(R'_a)_2$, $SC(R'_a)_2$ and $N(R'_a)C(R'_b)_2$, wherein $R'_a$ and $R'_b$ are each independently hydrogen or (1-8C)alkyl;
each R group is the same or different, each being independently selected from an aryl or heteroaryl group bearing a lone pair of electrons capable of coordinating with M or substituted by a group bearing a lone pair of electrons capable of coordinating with M;
wherein CORE or any R group is optionally further substituted by one or groups selected from halogeno, trifluoromethyl, trifluoromethoxy, cyano, isocyano, nitro, hydroxy, mercapto, amino, formyl, carboxy (incl. carboxylic acid), carbamoyl, ureido, sulphonyl (incl. sulphonic acid), phosphoryl (incl. phosphonic acid), (1-8C)alkyl, (2-8C)alkenyl, (2-8C)alkynyl, (1-8C)alkoxy,
(2-8C)alkenyloxy, (2-8C)alkynyloxy, (1-8C)alkylthio, (1-8C)alkylsulphinyl,
(1-8C)alkylsulphonyl, (1-8C)alkylamino, di-[(1-8C)alkyl]amino, (1-8C)alkoxycarbonyl,
N-(1-8C)alkylcarbamoyl, N,N-di-[(1-8C)alkyl]carbamoyl, (2-8C)alkanoyl,
(2-8C)alkanoyloxy, (2-8C)alkanoylamino, N-(1-8C)alkyl-(2-8C)alkanoylamino,
(3-6C)alkenoylamino, N-(1-6C)alkyl-(3-6C)alkenoylamino, (3-6C)alkynoylamino,
N-(1-6C)alkyl-(3-6C)alkynoylamino, N'-(1-6C)alkylureido, N',N'-di-[(1-6C)alkyl]ureido,
N-(1-6C)alkylureido, N,N'-di-[(1-6C)alkyl]ureido, N,N',N'-tri-[(1-6C)alkyl]ureido,
N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino;
or an (acceptable) salt and/or solvate thereof to selectively sorb the desired component within/to the sorbent material;
wherein the mixture of components comprises p-xylene and m-xylene.

* * * * *